US012562259B2

(12) United States Patent
Gulsun et al.

(10) Patent No.: US 12,562,259 B2
(45) Date of Patent: Feb. 24, 2026

(54) AI-BASED ANALYSIS OF CORONARY ANGIOGRAMS

(71) Applicant: SIEMENS HEALTHINEERS AG, Forchheim (DE)

(72) Inventors: Mehmet Akif Gulsun, Princeton, NJ (US); Vivek Singh, Princeton, NJ (US); Diana Ioana Stoian, Brasov (RO); Alexandru Constantin Serban, Constanta (RO); Puneet Sharma, Princeton Junction, NJ (US); Venkatesh Narasimha Murthy, Hillsborough, NJ (US)

(73) Assignee: Siemens Healthineers AG, Forchheim (DE)

( * ) Notice: Subject to any disclaimer, the term of this patent is extended or adjusted under 35 U.S.C. 154(b) by 406 days.

(21) Appl. No.: 18/310,601

(22) Filed: May 2, 2023

(65) Prior Publication Data

US 2024/0029868 A1     Jan. 25, 2024

Related U.S. Application Data

(60) Provisional application No. 63/368,889, filed on Jul. 20, 2022.

(30) Foreign Application Priority Data

Jul. 20, 2022    (EP) .................................... 22465546

(51) Int. Cl.
    *G16H 30/40*        (2018.01)
    *G06T 7/00*         (2017.01)
    *G16H 50/20*        (2018.01)

(52) U.S. Cl.
    CPC ........... *G16H 30/40* (2018.01); *G06T 7/0016* (2013.01); *G16H 50/20* (2018.01); *G06T 2207/10116* (2013.01); *G06T 2207/20081* (2013.01); *G06T 2207/20084* (2013.01); *G06T 2207/30048* (2013.01); *G06T 2207/30101* (2013.01)

(58) Field of Classification Search
    None
    See application file for complete search history.

(56) References Cited

U.S. PATENT DOCUMENTS

2023/0386184 A1*  11/2023  Duffy ....................... G06N 3/09

FOREIGN PATENT DOCUMENTS

CN        111657883 A   *  9/2020   ........... G06T 7/0012

OTHER PUBLICATIONS

English translation of CN-111657883-A. (Year: 2020).*
Du et al., "Training and validation of a deep learning architecture for the automatic analysis of coronary angiography", Coronary Interventions, 2020, EuroIntervention, 2021, pp. 32-40.

(Continued)

*Primary Examiner* — Thomas D Lee

(57)                ABSTRACT

Systems and methods for performing a medical imaging analysis task are provided. One or more input medical images of a patient are received. The one or more input medical images are encoded into embeddings using a machine learning based encoder network. A medical imaging analysis task is performed based on the embeddings. Results of the medical imaging analysis task are output.

21 Claims, 15 Drawing Sheets

100

(56)          References Cited

OTHER PUBLICATIONS

Du et al., "Automatic and multimodal analysis for coronary angiography: training and validation of a deep learning architecture", EuroIntervention, 2020, 45 pgs.

Iyer et al., "AngioNet: a convolutional neural network for vessel segmentation in X-ray angiography", Scientific Reports, 2021, 13 pgs.

Ma et al., "Transformer Network for Significant Stenosis Detection in CCTA of Coronary Arteries", arXiv:2107.03035v3, 2021, 10 pgs.

Gao et al., "Vessel segmentation for X-ray coronary angiography using ensemble methods with deep learning and filter-based features", BMC Medical Imaging, 2022, 17 pgs.

Yang et al., "Video Instance Segmentation", arXuv:1905.04804v4, 2019, pp. 1-10.

Pang et al., "Stenosis-DetNet: Sequence consistency-based stenosis detection for X-ray coronary angiography", Computerized Medical Imaging and Graphics, 2021, pp. 1-11.

Ronneberger et al., "U-Net: Convolutional Networks for Biomedical Image Segmentation", arXiv1505.04597v1, 2015, pp. 1-8.

Arbelle et al., "Microscopy Cell Segmentation Via Convolutional LSTM Networks", arXiv:1805.11247v2, 2019, 5 pgs.

Xu et al., "LSTM Multi-modal UNet for Brain Tumor Segmentation", IEEE 4th International Conference on Image, Vision and Computing, 2019, pp. 236-240.

Dosovitskiy et al., "An Image is Worth 16×16 Words: Transformers for Image Recognition at Scale", arXiv:2010.11929v2, 2021, pp. 1-22.

Sarlin et al., "SuperGlue: Learning Feature Matching with Graph Neural Networks", Proceedings of the IEEE/CVF Conference on Computer Vision and Pattern Recognition, 2020, pp. 4938-4947.

Germain et al., Visual Correspondence Hallucination, arXiv:2106.09711v3, 2022, 28 pgs.

U.S. Appl. No. 17/655,089, "Multi-View Matching Across Coronary Angiograms", filed Mar. 16, 2022, 39 pgs.

U.S. Appl. No. 17/934,213, "A Multi-Task Learning Framework for Fully Automated Assessment of Coronary Arteries in Angio Images", filed Sep. 22, 2022, 37 pgs.

* cited by examiner

Figure 1:
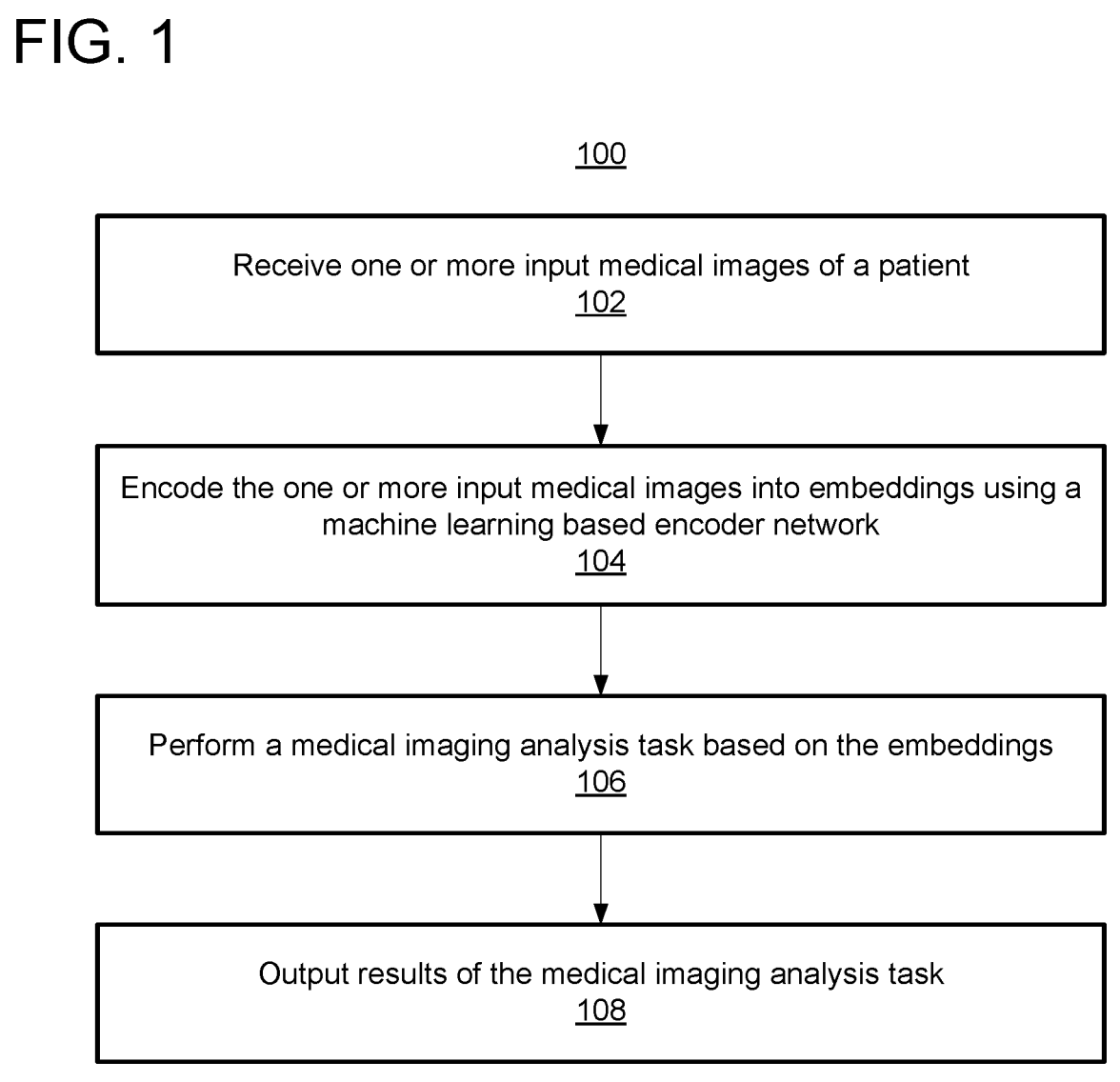

Receive one or more input medical images of a patient
102

Encode the one or more input medical images into embeddings using a machine learning based encoder network
104

Perform a medical imaging analysis task based on the embeddings
106

Output results of the medical imaging analysis task
108

FIG. 2

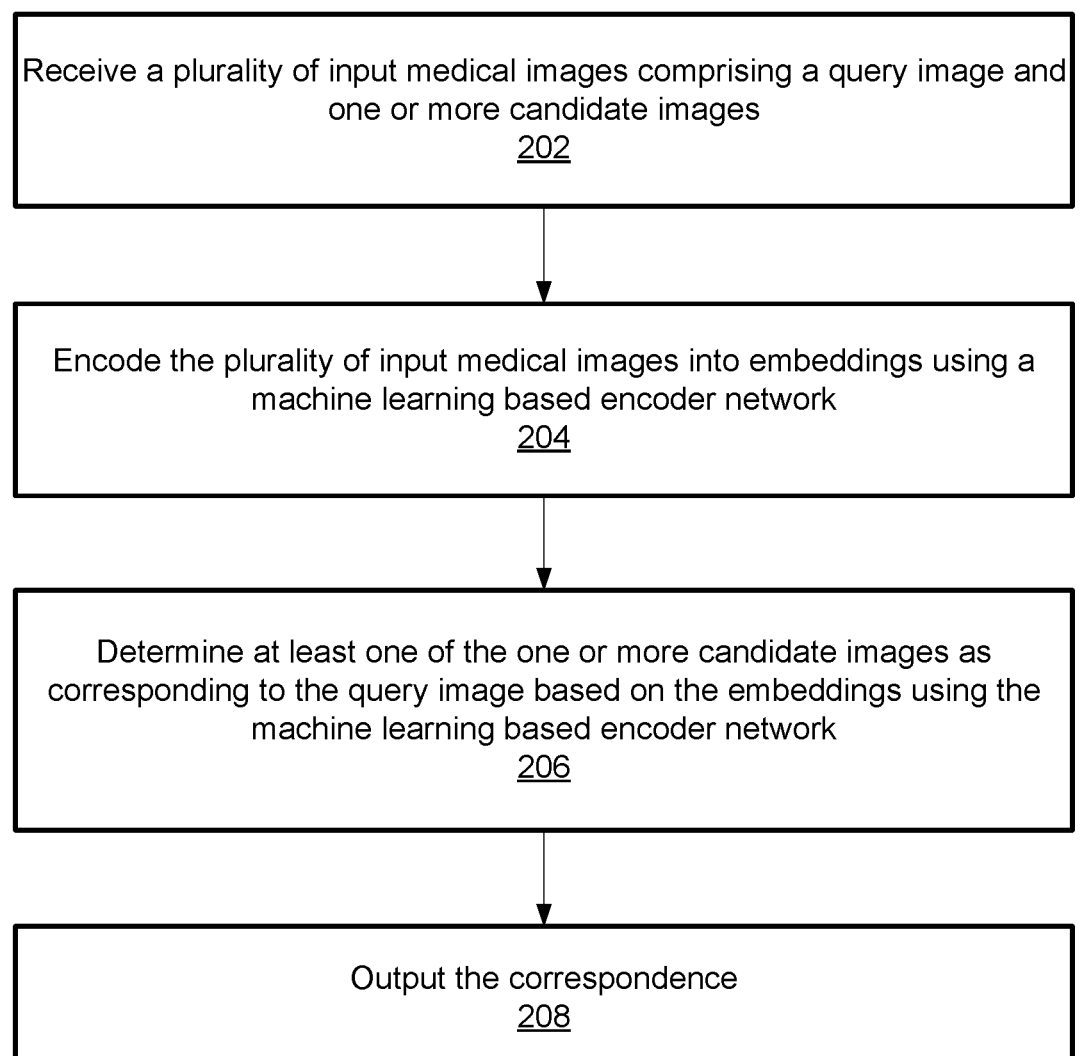

200

Receive a plurality of input medical images comprising a query image and one or more candidate images
202

Encode the plurality of input medical images into embeddings using a machine learning based encoder network
204

Determine at least one of the one or more candidate images as corresponding to the query image based on the embeddings using the machine learning based encoder network
206

Output the correspondence
208

Figure 6:
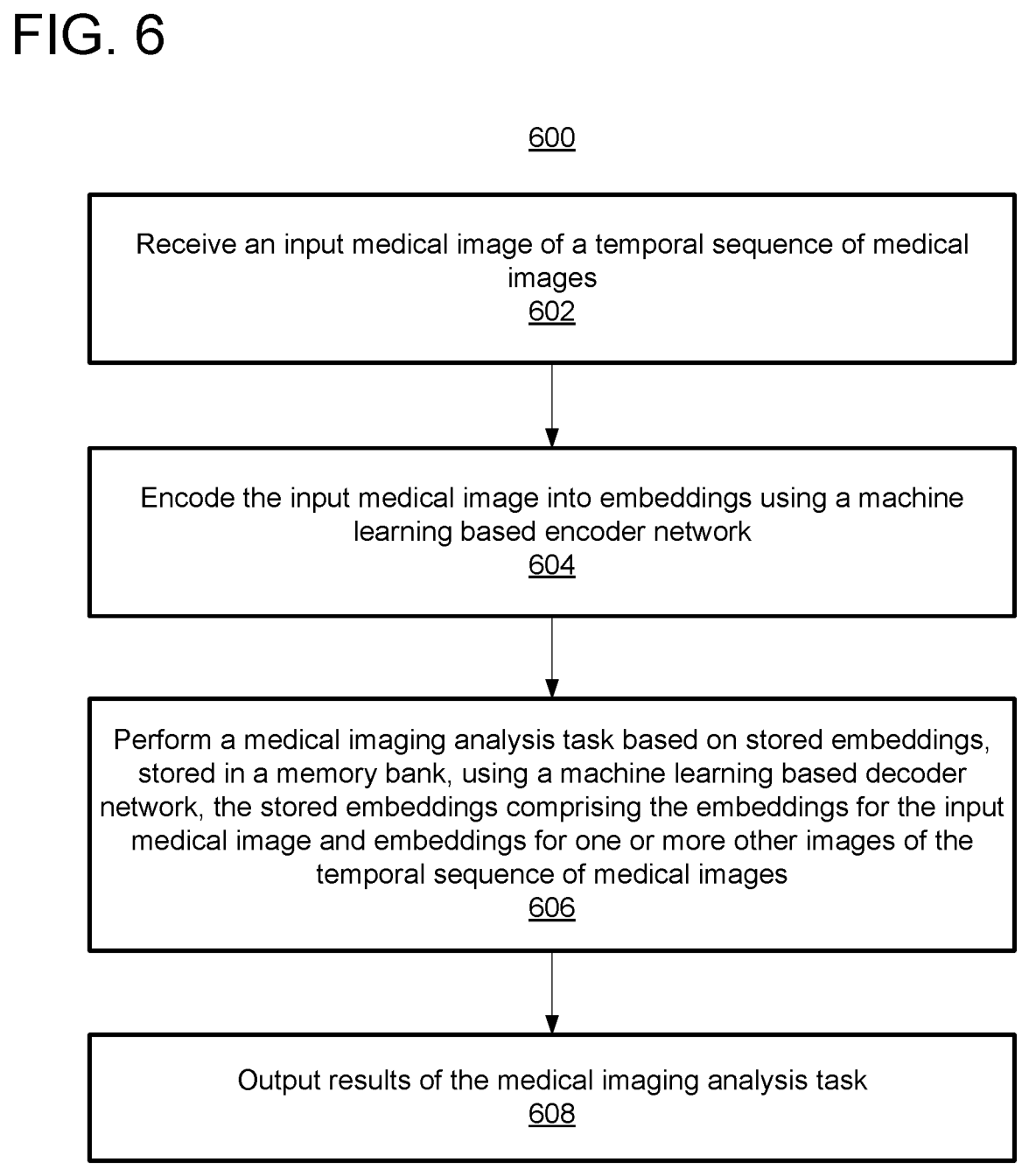

Receive an input medical image of a temporal sequence of medical images
602

Encode the input medical image into embeddings using a machine learning based encoder network
604

Perform a medical imaging analysis task based on stored embeddings, stored in a memory bank, using a machine learning based decoder network, the stored embeddings comprising the embeddings for the input medical image and embeddings for one or more other images of the temporal sequence of medical images
606

Output results of the medical imaging analysis task
608

FIG. 8

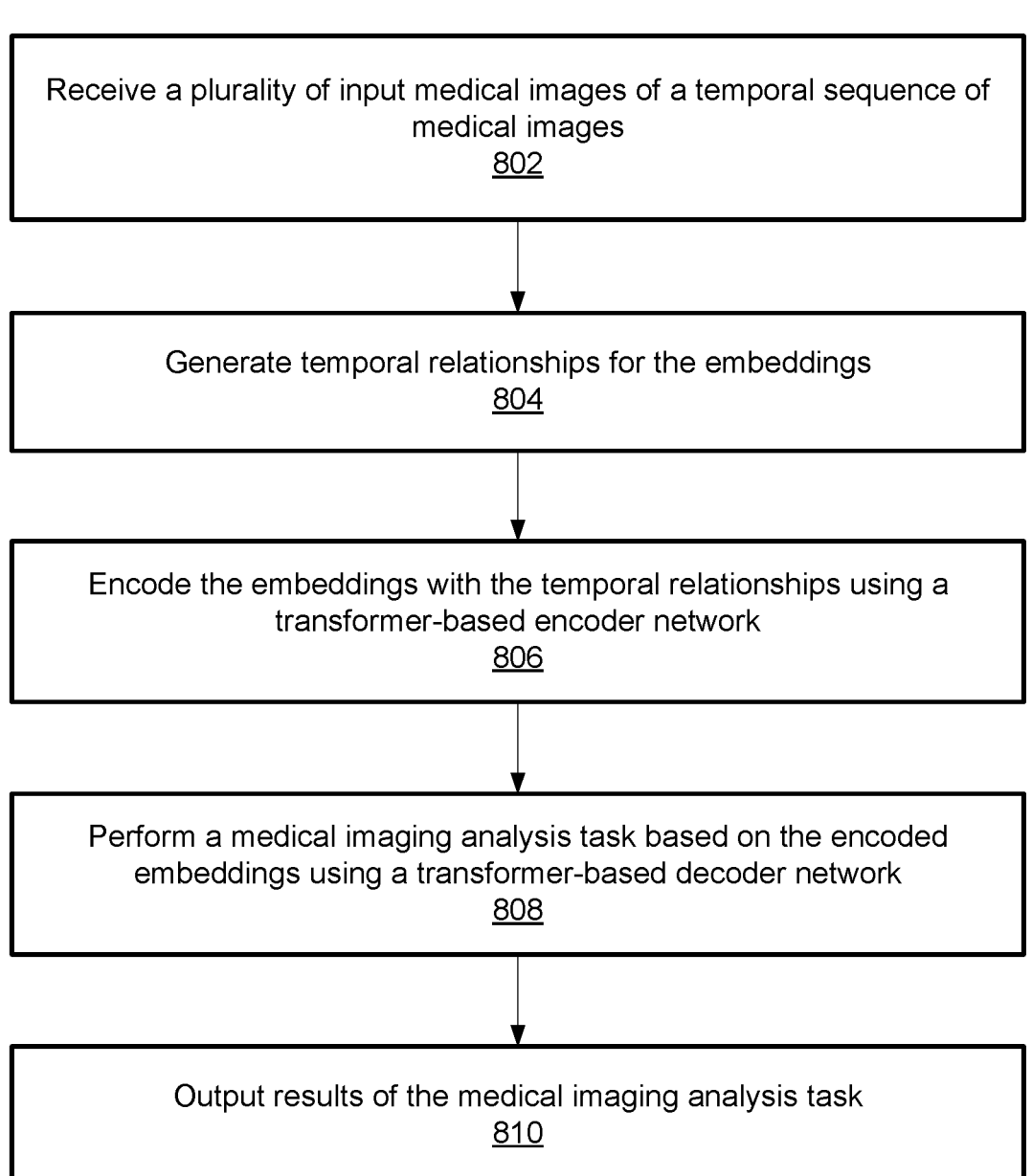

800

Receive a plurality of input medical images of a temporal sequence of medical images
802

Generate temporal relationships for the embeddings
804

Encode the embeddings with the temporal relationships using a transformer-based encoder network
806

Perform a medical imaging analysis task based on the encoded embeddings using a transformer-based decoder network
808

Output results of the medical imaging analysis task
810

FIG. 10

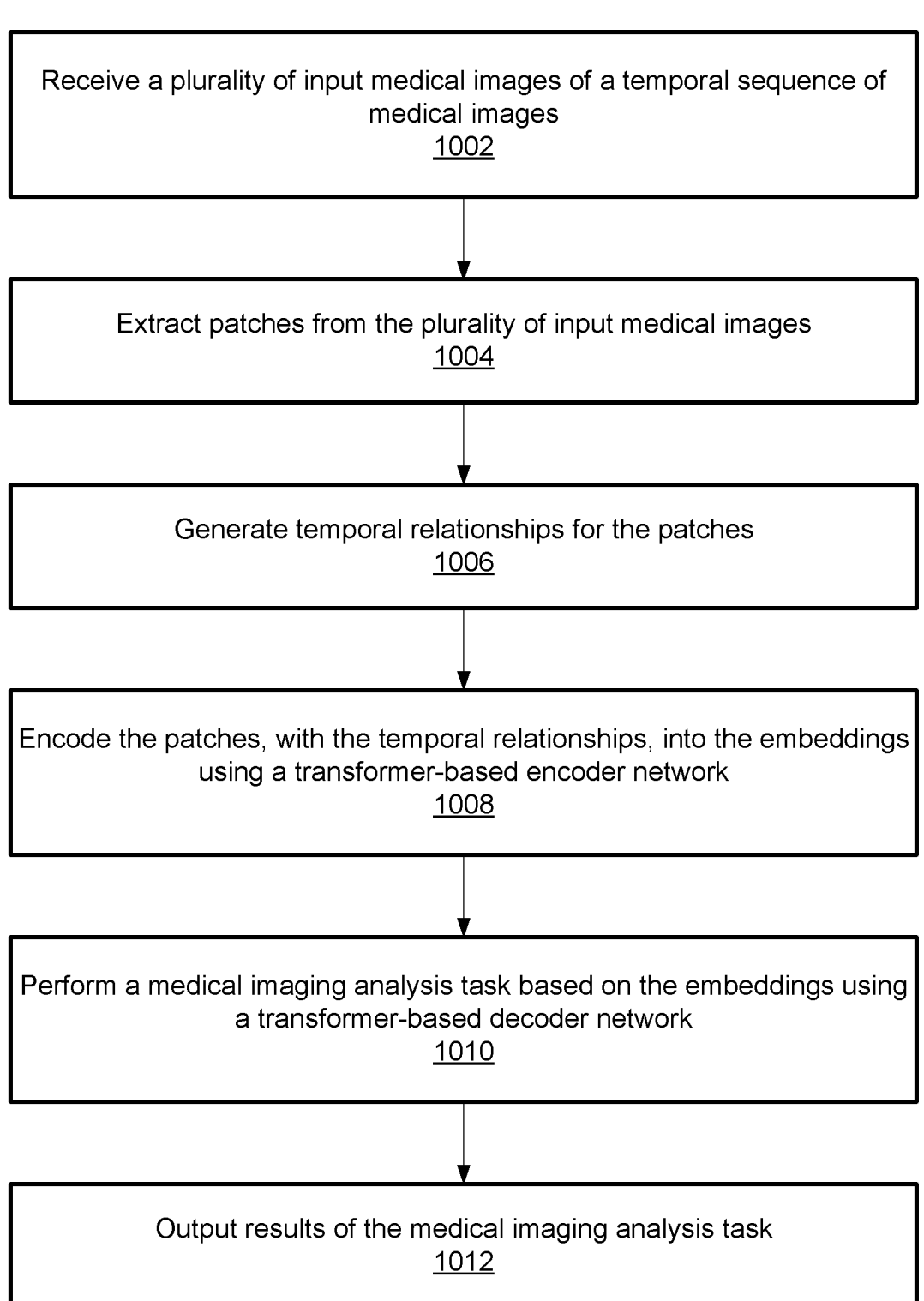

1000

Receive a plurality of input medical images of a temporal sequence of medical images
1002

Extract patches from the plurality of input medical images
1004

Generate temporal relationships for the patches
1006

Encode the patches, with the temporal relationships, into the embeddings using a transformer-based encoder network
1008

Perform a medical imaging analysis task based on the embeddings using a transformer-based decoder network
1010

Output results of the medical imaging analysis task
1012

AI-BASED ANALYSIS OF CORONARY ANGIOGRAMS

CROSS-REFERENCE TO RELATED APPLICATIONS

This application claims the benefit of U.S. Provisional Application No. 63/368,889, filed Jul. 20, 2022, and European Patent Application No. EP 22465546.4, filed Jul. 20, 2022, the disclosures of which are herein incorporated by reference in their entirety.

TECHNICAL FIELD

The present invention relates generally to AI (artificial intelligence)/ML (machine learning), and in particular to AI-based analysis of coronary angiograms.

BACKGROUND

A coronary angiography is a procedure to visualize blood flow through arteries of the heart. In clinical practice, coronary angiographies are performed by injecting a contrast agent into the coronary artery vessels and imaging the vessels using x-rays for diagnostic reporting and intervention planning. Conventional techniques have been proposed for automatic analysis of coronary angiography images. However, since the contrast agent propagates through the vessels while imaging, the contrast levels in the coronary artery vessels vary across temporal frames of the angiography sequence, which may reduce the performance of such conventional coronary angiography image analysis techniques. In addition, cardiac and breathing motion of the patient may result in overlapping branches in the coronary angiography images, which may also reduce the performance of such conventional coronary angiography image analysis techniques. Patient, sensor, and table motion may also cause movement of some branches of the coronary artery to partially move outside of the image field of view, which may further reduce the performance of such conventional coronary angiography image analysis techniques.

BRIEF SUMMARY OF THE INVENTION

Embodiments described herein provide for improved methods and systems for automatic analysis of coronary angiography images using AI-based analyses. In one embodiment, methods and systems for determining corresponding coronary angiography images are provided. In another embodiment, methods and systems for performing a medical imaging analysis task on coronary angiography images based on temporal relationships between the coronary angiography images are provided.

In accordance with one or more embodiments, systems and methods for performing a medical imaging analysis task are provided. One or more input medical images of a patient are received. The one or more input medical images are encoded into embeddings using a machine learning based encoder network. A medical imaging analysis task is performed based on the embeddings. Results of the medical imaging analysis task are output.

In one embodiment, patches are extracted from the plurality of input medical images. The patches are encoded into the embeddings based on one or more of spatial, temporal, anatomical, cardiac phase, and angulation information extracted from the one or more input medical images using a transformer-based encoder network.

In one embodiment, the one or more input medical images comprise a plurality of input medical images comprising a query image and one or more candidate images. The medical imaging analysis task is performed by determining at least one of the one or more candidate images as corresponding to the query image based on the embeddings using the machine learning based encoder network. In one embodiment, matching scores between the embeddings are generated using the machine learning based encoder network. In one embodiment, the embeddings for the one or more candidate images are ranked based on a similarity to the embeddings for the query image using the machine learning based encoder network.

In one embodiment, the one or more input medical images comprise an input medical image of a temporal sequence of medical images. The medical imaging analysis task is performed based on stored embeddings, stored in a memory bank, using a machine learning based decoder network. The stored embeddings comprise the embeddings for the input medical image and embeddings for one or more other images of the temporal sequence of medical images. The machine learning based encoder network and the machine learning based decoder network are trained based on a consistency loss measuring temporal consistency between training images.

In one embodiment, the one or more input medical images comprise a plurality of input medical images of a temporal sequence of medical images. Temporal relationships are generated for the embeddings. The embeddings are encoded with the temporal relationships using a transformer-based encoder network. The medical imaging analysis task is performed based on the encoded embeddings using a transformer-based decoder network.

In one embodiment, the one or more input medical images comprise a plurality of input medical images of a temporal sequence of medical images. Patches are extracted from the plurality of input medical images. Temporal relationships are generated for the patches. The patches are encoded, with the temporal relationships, into the embeddings using a transformer-based encoder network. The medical imaging analysis task is performed based on the embeddings using a transformer-based decoder network.

In one embodiment, the one or more input medical images are coronary angiography images of the patient.

These and other advantages of the invention will be apparent to those of ordinary skill in the art by reference to the following detailed description and the accompanying drawings.

BRIEF DESCRIPTION OF THE DRAWINGS

FIG. 1 shows a method for performing a medical imaging analysis task, in accordance with one or more embodiments;

FIG. 2 shows a method for determining corresponding images in a plurality of input medical images, in accordance with one or more embodiments;

FIG. 6 shows a method for performing a medical imaging analysis task with temporal consistency using CNN based networks, in accordance with one or more embodiments;

FIG. 8 shows a method for performing a medical imaging analysis task with temporal consistency using CNN and transformer-based networks, in accordance with one or more embodiments;

FIG. 10 shows a method for performing a medical imaging analysis task with temporal consistency using transformer-based networks, in accordance with one or more embodiments;

FIG. 11 shows a framework training transformer-based encoder and decoder networks for performing segmentation, in accordance with one or more embodiments;

DETAILED DESCRIPTION

Figure 3:
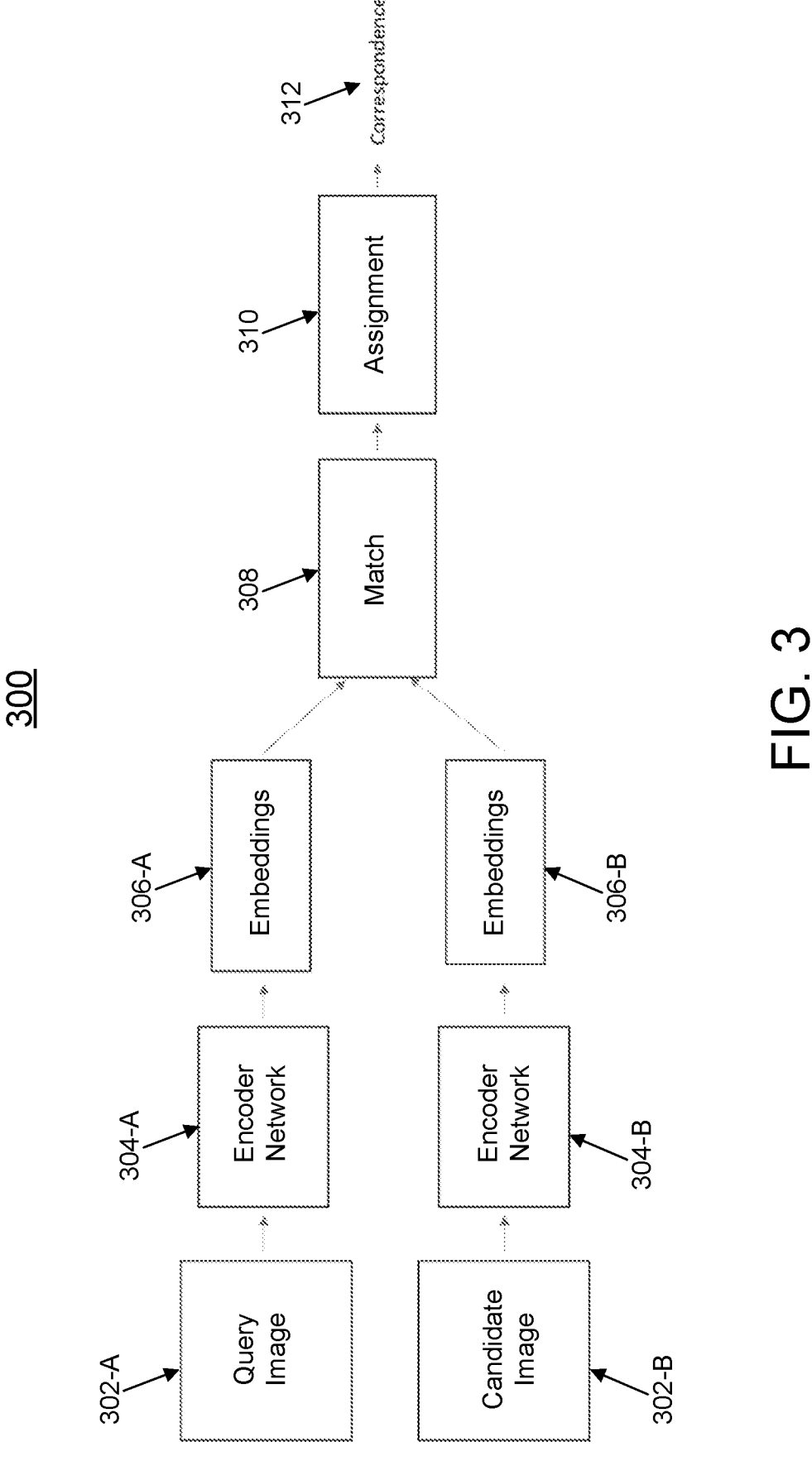
FIG. 3 shows a workflow for determining corresponding images in a plurality of input medical images, in accordance with one or more embodiments.

The present invention generally relates to methods and systems for AI-based analysis of coronary angiograms. Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Coronary angiographies are performed to visualize blood flow through arteries of the heart. Conventional techniques for the automatic analysis of coronary angiography images may have reduced performance due to, for example, varying contrast levels in the coronary artery vessels across temporal frames of an angiography sequence, cardiac and breathing motion of the patient, and patient and table motion during the procedure.

Embodiments described herein provide for improved methods and systems for performing a medical imaging analysis task on coronary angiography images with temporal consistency. Coronary angiography images may be temporally inconsistent due to, e.g., cardiac and breathing motion of the patient and patient, sensor, and table motion during a procedure. Advantageously, such medical imaging analysis tasks are performed in accordance with embodiments described herein with significantly improved temporal consistency between results of the medical imaging analysis tasks. In one or more embodiments, methods and systems for determining corresponding coronary angiography images are provided. Such corresponding coronary angiography images may be used for downstream automatic analysis tasks with improved performance, as well as a guidance tool for manual analysis tasks performed by radiologists. In one or more embodiments, methods and systems for performing a medical imaging analysis task on coronary angiography images based on temporal relationships between the coronary angiography images are provided.

FIG. 1 shows a method 100 for performing a medical imaging analysis task, in accordance with one or more embodiments. The steps of method 100 may be performed by one or more suitable computing devices, such as, e.g., computer 1502 of FIG. 15. In one or more embodiments, method 100 may be performed for determining corresponding images, as described below with respect to FIGS. 2-5. In one or more embodiments, method 100 may be performed to perform the medical imaging analysis task on medical images based on temporal relationships between the medical images, as described below with respect to FIGS. 6-12.

At step 102 of FIG. 1, one or more input medical images of a patient are received. In one embodiment, the input medical images may be of the coronary artery vessels of the patient. However, the input medical images may be of any anatomical object(s) of the patient, such as, e.g., an organ, a vessel, a tumor, and/or any other anatomical object of interest.

In one embodiment, the input medical images are coronary angiography images acquired via x-ray using a contrast agent (e.g., iodine or barium). The coronary angiography images may be of different views or angles of the vessels or may be a temporal sequence of images of the vessels. However, the input medical images be of any other suitable modality, such as, e.g., MRI (magnetic resonance imaging), CT (computed tomography), US (ultrasound), x-ray, or any other medical imaging modality or combinations of medical imaging modalities. The input medical images may be 2D (two-dimensional) images and/or 3D (three-dimensional) volumes. Accordingly, reference herein to pixels of a 2D image apply equally to voxels of a 3D volume and vice versa. In some embodiment, the input medical images may be patches extracted from a medical image. The input medical images may be received directly from an image acquisition device (e.g., image acquisition device 1514 of FIG. 15), such as, e.g., an X-ray scanner, as the medical images are acquired, or can be received by loading previously acquired medical images from a storage or memory of a computer system, or can be received from a remote computer system.

At step 104 of FIG. 1, the one or more input medical images are encoded into embeddings using a machine learning based encoder network. The encoder network receives as input the input medical images and generates as output embeddings for each respective input medical image. The embeddings are relatively low-dimensional vector representations of the respective input medical image.

In one embodiment, the encoder network may be implemented as a CNN (convolutional neural network) based encoder or a vision transformer encoder implemented as a masked autoencoder or variational autoencoder or any other deep network. However, the encoder network may be implemented using any suitable machine learning based architecture. The encoder network is trained together with a decoder network during a prior offline or training phase. Once trained, the trained encoder network is applied during an online or inference stage (e.g., at step 104 of FIG. 1).

At step 106 of FIG. 1, a medical imaging analysis task is performed based on the embeddings. In one or more embodiments, the one or more input medical images comprise a plurality of input medical images and the medical imaging analysis task comprises determining corresponding images between two or more of the plurality of input medical images. In one or more embodiments, the medical imaging analysis task comprises classification, detection, segmentation, or any other suitable medical imaging analysis task performed based on temporal relationships between the one or more input medical images. However, the medical imaging analysis task may comprise any other suitable medical imaging analysis task.

At step 108 of FIG. 1, results of the medical imaging analysis task are output. For example, the results of the medical imaging analysis task can be output by displaying the results on a display device of a computer system, storing the results on a memory or storage of a computer system, or by transmitting the results to a remote computer system.

In one or more embodiments, method 100 of FIG. 1 may be performed for determining correspondences between two or more of a plurality of input medical images, as described with respect to FIGS. 2-5.

FIG. 2 shows a method 200 for determining corresponding images in a plurality of input medical images, in accordance with one or more embodiments. The steps of method 200 may be performed by one or more suitable computing devices, such as, e.g., computer 1502 of FIG. 15. FIG. 3 shows a workflow 300 for determining corresponding images in a plurality of input medical images, in accordance with one or more embodiments. FIGS. 2 and 3 will be discussed together, with continued reference to FIG. 1.

At step 202 of FIG. 2, a plurality of input medical images comprising a query image and one or more candidate images is received. Step 202 of FIG. 2 corresponds to step 102 of FIG. 1. In one example, as shown in workflow 300 of FIG. 3, the query image and the one or more candidate images are query image 302-A and candidate image 302-B (collectively referred to as images 302) respectively. Images 302 may depict different views or angles of the anatomical object of interest and/or may be different images (acquired at different points in time) of a temporal sequence of medical images of the anatomical object. In one embodiment, each image 302 may comprise a multi-channel image, where each channel corresponds to image data at different resolutions. In one embodiment, images 302 are patches extracted from one or more images. The patches may be overlapping or non-overlapping.

At step 204 of FIG. 2, the plurality of input medical images is encoded into embeddings using a machine learning based encoder network. Step 204 of FIG. 2 corresponds to step 104 of FIG. 1. In one example, as shown in workflow 300 of FIG. 3, images 302 are respectively encoded into embeddings 306-A and 306-B (collectively referred to as embeddings 306) using a machine learning based encoder network 304-A and 304-B (collectively referred to as encoder network 304). While encoder networks 304-A and 304-B are separately shown in workflow 300 to illustrate encoding of input medical images 302, it should be understood that encoder networks 304-A and 304-B are the same encoder network 304. In one embodiment, encoder network 304 is a deep learning based encoder network, such as, e.g., a vision transformer encoder implemented as a masked autoencoder or variational autoencoder. Encoder network 304 is trained during a prior offline or training stage. Once trained, the trained encoder network 304 is applied, e.g., at step 104 of FIG. 1 or step 204 of FIG. 2 to encode images into embeddings. In one embodiment, encoder network 304 is trained according to framework 400 of FIG. 4.

Figure 4:
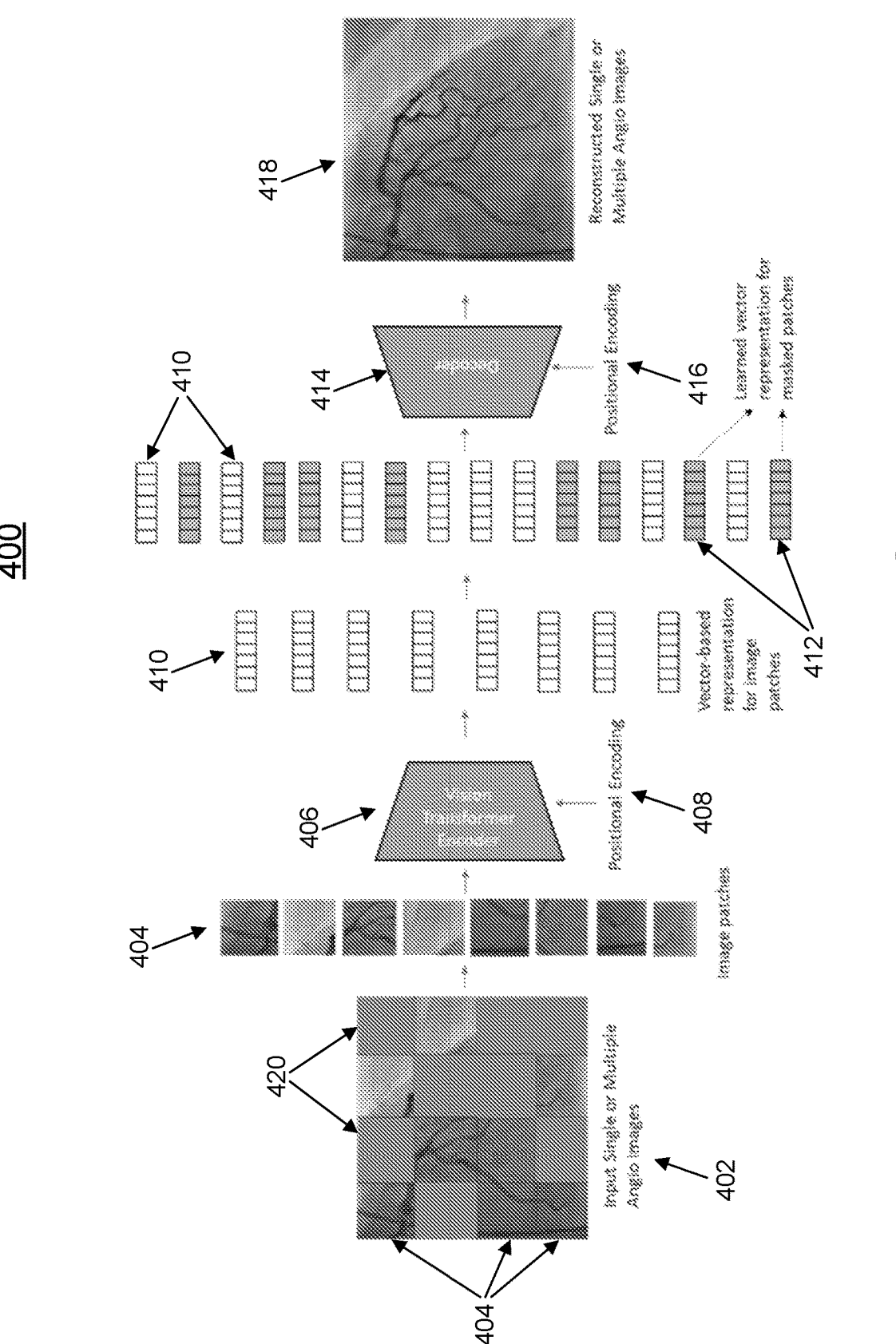
FIG. 4 shows a framework for training a masked autoencoder network, in accordance with one or more embodiment.

FIG. 4 shows a framework 400 for training a masked autoencoder network, in accordance with one or more embodiment. Framework 400 comprises vision transformer encoder 406 and decoder 414. Framework 400 is performed during a prior offline or training stage for training vision transformer encoder 406. Once trained, the trained vision transformer encoder 406 is applied during an online or inference stage, e.g., to perform step 104 of FIG. 1 or step 204 of FIG. 2. Decoder 414 is used during the training phase for training vision transformer encoder 406 and is not used during the inference stage. In one example, vision transformer encoder 406 is the machine learning based encoder network applied at step 104 of FIG. 1, the machine learning based encoder network applied at step 204 of FIG. 2, or encoder network 304 of FIG. 3.

Framework 400 comprises one or more training images 402 (e.g., angiography images). Training images 402 comprise image patches 404 and masked patches 420. Image patches 404 are extracted from training images 402 and input into vision transformer encoder 406. Vision transformer encoder 406 learns to encode image patches 404 based on positional encoding 408 to respectively generate as output embeddings 410 (shown as not shaded in FIG. 4) and learned embeddings 412 (shown as shaded in FIG. 4). Each of the embeddings 410 are a vector-based representation for a respective image patch 404. Each of the learned embeddings 412 are a learned vector-based representation for a respective masked patch 420. Decoder 414 learns to decode embeddings 410 and learned embeddings 412 based on positional encoding 416 to generate reconstructions of training images 402 as reconstructed images 418.

Referring back to method 200 of FIG. 2, at step 206, at least one of the one or more candidate images are determined as corresponding to the query image based on the embeddings using the machine learning based encoder network. Step 206 of FIG. 2 corresponds to step 106 of FIG. 1. In one example, as shown in workflow 300 of FIG. 3, correspondence estimation (or patch matching) is performed to determine a match 310 between embeddings 306-A and 306-B for query image 302-A and candidate image 302-B respectively. For example, match 310 may be determined as matching scores representing a correspondence of query image 302-A and candidate image 302-B. In another example, correspondence estimation is performed by ranking embeddings 306-B for the one or more candidate images 302-B based on their proximity or similarity to embeddings 306-A for query image 302-A. The correspondence indicates that query image 302-A and candidate image 302-B depict a same region (e.g., same cardiac region) of the patient.

In one embodiment, correspondence estimation is performed by encoder network 304 using a Siamese like architecture. Encoder network 304 is first applied to extract embeddings 306 from images 302 and subsequently trained to predict whether the images 302 correspond to the same region of the patient. The trained encoder network 304 receives as input embeddings 306 and generates as output matching scores 308. An assignment 310 defining a correspondence between the query image 302-A and candidate image 302-B is then made based on match 308.

In one embodiment, encoder network 304 is trained by sampling several pairs of training images, where each pair may be a valid or an invalid correspondence, and training the encoder network 304 to minimize a matching loss function (e.g., a discriminative loss or contrast loss). In another embodiment, encoder network 304 is trained by sampling a patch from query image 302-A and a set of patches from candidate image 302-B and training encoder network 304 to rank candidate patches based on their proximity or similarity to the query patch based on embeddings 306 using a ranking loss, as shown in framework 500 of FIG. 5.

Figure 5:
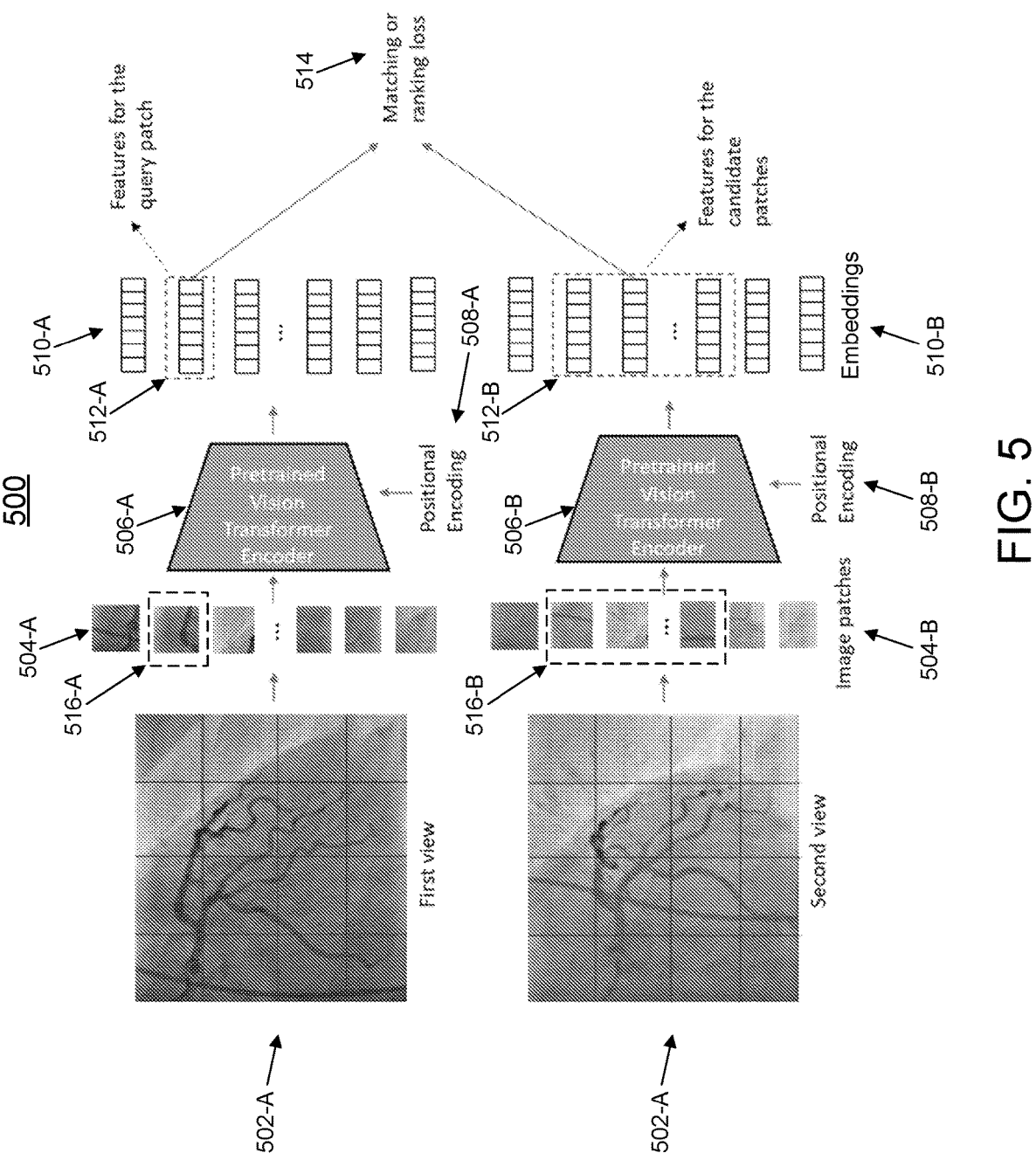
FIG. 5 shows a framework for training an encoder network for determining corresponding images, in accordance with one or more embodiments.

FIG. 5 shows a framework 500 for training an encoder network for determining corresponding images, in accordance with one or more embodiments. Framework 500 is performed during a prior offline or training stage for training pretrained vision transformer encoders 506-A and 506-B. While separately shown in framework 500 to illustrate processing of training images 502-A and image 502-B (collectively referred to as training images 502), it should be understood that pretrained vision transformer encoders 506-A and 506-B are the same pretrained vision transformer encoder 506. Once trained, the trained vision transformer encoder 506 is applied during an online or inference stage, e.g., to perform step 106 of FIG. 1 or step 206 of FIG. 2. In one example, pretrained vision transformer encoder 506 is the machine learning based encoder network utilized at steps 104 and (in some embodiments) 106 of FIG. 1, the machine learning based encoder network utilized at steps 204 and (in some embodiments) 206 of FIG. 2, or encoder network 304 in FIG. 3.

As shown in framework 500, image patches 504-A and 504-B (collectively referred to as image patches 504) are respectively extracted from training images 502 and input into pretrained vision transformer encoder 506. Pretrained vision transformer encoder 506 encodes image patches 504 based on positional encoding 508-A and 508-B to respectively generate embeddings 510-A and 510 (collectively referred to as embeddings 510). Embeddings 510-A comprise embeddings (or features) 512-A for a query patch 516-A (designated from image patches 504-A) and a set of embeddings 512-B for a plurality of candidate patches 516-B (designated from image patches 510-B). Pretrained vision transformer encoder 506 is trained to rank the plurality of candidate patches based on their proximity or similarity to the query patch based on a matching or ranking loss 514.

Referring back to method 200 of FIG. 2, at step 208, the correspondence is output. Step 208 of FIG. 2 corresponds to step 108 of FIG. 1. In one example, as shown in workflow 300 of FIG. 3, correspondence 312 is output.

Advantageously, the encoder networks utilized in method 200 may be implemented as vision transformer-based patch descriptors that may be pretrained on large amounts of data using self-supervision for improved performance. Method 200 enables the leveraging of multi-view temporal data for improved automated assessment, consistent results across multi-view temporal images, and matching findings such as, e.g., stenosis detections.

The correspondences determined according to method 200 may be utilized in various downstream medical imaging analysis tasks. For example, in one or more embodiments, the correspondences may be utilized in: 1) centerline tracing based on a multi-view and temporal cost metric in order to improve results (e.g., robustness to shortcuts), 2) object tracking across multiple views and temporal frames, 3) matching automatically detected findings such as, e.g., a stenosis grade, across multiple views and temporal frames in order to perform aggregation, 4) ranking views/images with a best diagnostic quality for a specific segment (based on a manual or automated quality score), and/or 5) supporting human experts (e.g., hovering the mouse cursor on a specific angiography image can highlight corresponding regions in other images).

In one embodiment, the correspondences determined according to method 200 may be utilized to track stenosis findings detected on multiple views or temporal images to improve detection accuracy. For example, in one embodiment, false positive stenosis detections on certain images may be removed. First, stenosis masks and bounding boxes are computed by applying a threshold to stenosis heatmaps detected in multiple images. Stenosis bounding boxes from each image are then tracked to all other images based on correspondences (determined according to method 200 of FIG. 2). A score map for each particular image is obtained by aggregating all bounding boxes on the particular image. For example, a pixel can be assigned with a score based on a frequency or count of bounding boxes that contain that pixel. A detected stenosis is considered to be a false positive and removed if the, e.g., maximum, mean, or median score in its mask/bounding box is below a threshold.

In one embodiment, method 200 is performed over a plurality of images such that the encoder network generates embeddings not only based on the query image and the candidate images, but also based on neighboring images.

In one embodiment, instead of matching one query image at a time, correspondences for several query images may be simultaneously determined. For a set of query patches from the query image, a set of candidate patches from the candidate image is first obtained along with a likelihood of corresponding to the set of query patches. Next, a candidate patch is identified as matching with a query patch by solving an assignment problem, such as, one-one assignment using the Hungarian algorithm or max-flow min-cut or one to many assignment to find the assignment which maximizes the aggregate correspondence likelihood. To ensure topological consistency of the established correspondences, patch matching may be performed using a graph-based representation, where the patches are represented by nodes connected via edges to neighboring patches based on the positional and/or temporal encoding.

In one embodiment, synthesized DRR (digitally reconstructed radiograph) images from CTA (CT angiography) can be used for pretraining the encoder network. The synthesized DRR images may be augmented by applying motion (e.g., cardiac motion, breathing motion, patient motion, table motion, etc.) to CTA coronaries or by perturbing the topology of the CTA coronaries to mimic contrast filling.

In one embodiment, angulation may be embedded in the positional encoding, in addition to the spatial position, to leverage the projection geometry.

In one or more embodiments, method 100 of FIG. 1 may be performed for performing a medical imaging analysis task (e.g., classification, detection, segmentation) based on temporal relationships between the one or more input medical images, as described with respect to FIGS. 6-12.

Figure 7:
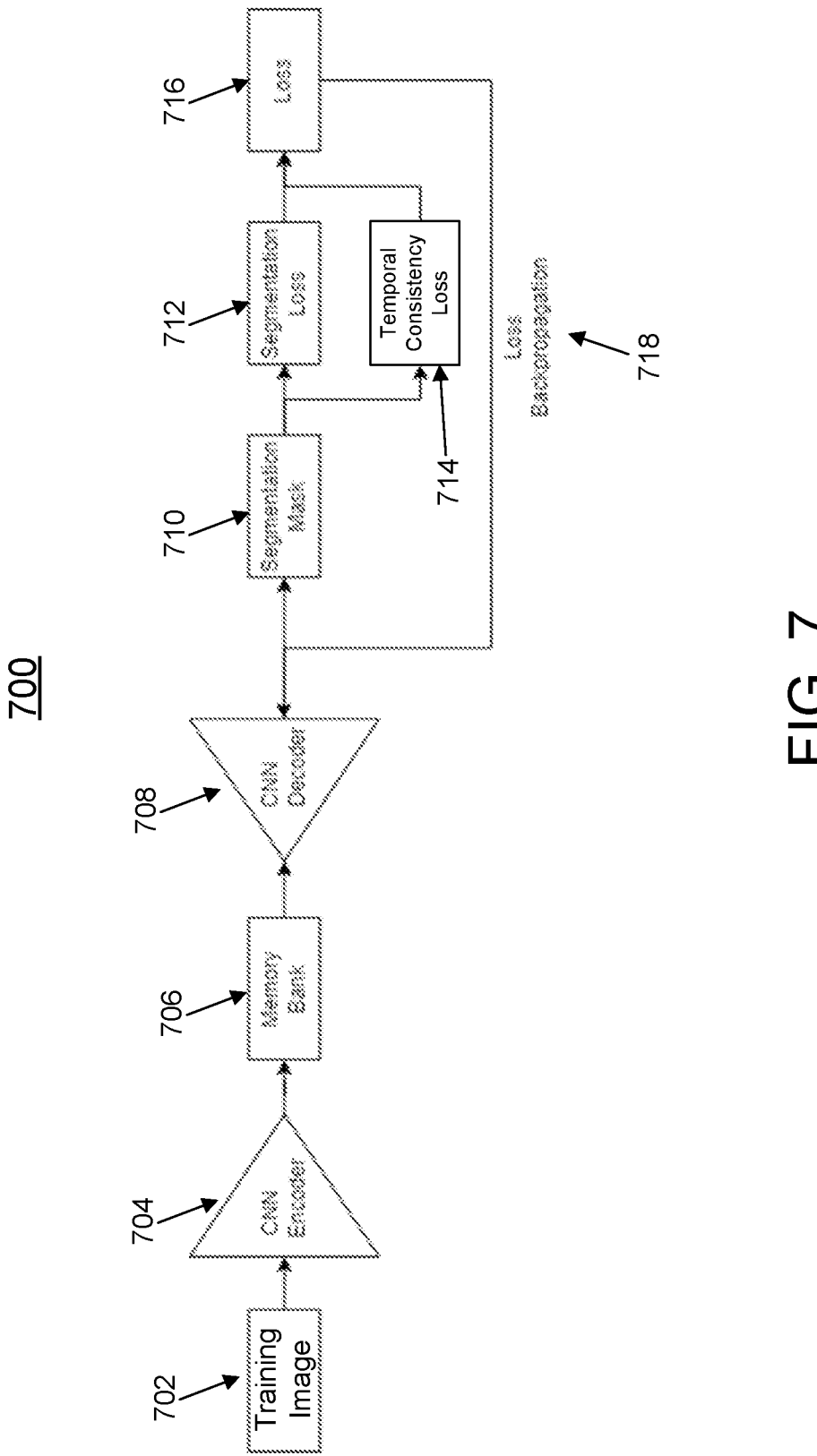
FIG. 7 shows a framework training a CNN based encoder network and decoder network for performing temporally consistent segmentation, in accordance with one or more embodiments.

FIGS. 6-12 show embodiments for performing a medical imaging analysis task based on temporal relationships. In one embodiment, the input data in the embodiments shown in FIGS. 6-12 is a temporal sequence of medical images comprising one or more images acquired before a contrast agent is visible and one or more images with the contrast agent visible. Each of the embodiments of FIGS. 6-12 are based on the following methodology. First, the medical imaging analysis task is performed using machine learning networks that maintains the temporal consistency of the sequence of medical images using, e.g., a memory bank (as shown in FIGS. 6-7) or transformer networks (as shown in FIGS. 8-11). Second, the sequence of medical images is encoded to embeddings that can be used for performing the medical imaging analysis task. Third, the embeddings are decoded using a task-specific decoder network. Fourth, the temporal consistency of the sequence of medical images is optimized with a task-specific loss using a dedicated loss function that takes into account both frame-to-frame, progressive, and motion divergence. The frame-to-frame, progressive, and motion divergence is addressed by modeling and embedding the ordered sequency of medical images and by using a dedicated temporal consistency loss term in the loss function that optimizes temporal consistency. Advantageously, motion artifacts, e.g., due to cardiac and breathing motion of the patient, and patient and table motion during a procedure, are better understood and corrected by the machine learning networks. Further, the impact of any devices present in the medical images can be restricted using input frames without contrast agent (and implicitly modelling their temporal consistency, encouraging the networks to learn that the devices that appeal in later images should not be considered for the task).

FIG. 6 shows a method 600 for performing a medical imaging analysis task with temporal consistency using CNN based networks, in accordance with one or more embodiments. The steps of method 600 may be performed by one or more suitable computing devices, such as, e.g., computer 1502 of FIG. 15.

At step 602 of FIG. 6, an input medical image of a temporal sequence of medical images is received. Step 602 of FIG. 6 corresponds to step 102 of FIG. 1.

At step 604 of FIG. 6, the input medical image is encoded into embeddings using a machine learning based encoder network. Step 604 of FIG. 6 corresponds to step 104 of FIG. 1. A memory bank stores the embeddings for the input medical image, as well as embeddings for one or more other images of the temporal sequence of medical images. Such other images were previously encoded by the encoder network during one or more prior iterations. The memory bank may be implemented as a RNN (recurrent neural network), such as, e.g., an LSTM (long short-term memory) network, or any other suitable memory bank.

At step 606 of FIG. 6, a medical imaging analysis task is performed based on stored embeddings, stored in the memory bank, using a machine learning based decoder network. The stored embeddings comprise the embeddings for the input medical image and embeddings for one or more other images of the temporal sequence of medical images. Step 606 of FIG. 6 corresponds to step 106 of FIG. 1. The medical imaging analysis task may comprise detection, classification, segmentation, or any other suitable medical imaging analysis task. The decoder network receives as input the embeddings for the input medical image and the embeddings for one or more other images and generates as output results of the medical imaging analysis task (e.g., a segmentation mask). The encoder network and the decoder network may be implemented according to a U-Net architecture or any other suitable machine learning based architecture. The encoder network and the decoder network are trained during a prior offline or training stage, e.g., according to framework 700 of FIG. 7. Once trained, the trained encoder network and the trained decoder network are applied during an online or inference stage, e.g., to perform steps 104 and 106 of FIG. 1 or steps 604 and 606 of FIG. 6.

At step 608 of FIG. 6, results of the medical imaging analysis task are output. Step 608 of FIG. 6 corresponds to step 108 of FIG. 1.

Advantageously, the memory bank is implemented for only storing embeddings following the encoder network but before the decoder network, instead of implementing the memory bank after the decoder network or after each convolutional layer of the encoder network. By modeling temporal consistency using the memory bank, method 600 provides for faster training speed and parallelization of the encoder network and decoder network, as only the memory bank uses LSTM cells (in some embodiments) which are not parallelizable. Method 600 also provides for better generalization to other medical imaging analysis tasks, since method 100 does not enforce a specific architecture of the decoder network.

FIG. 7 shows a framework 700 training a CNN based encoder network and decoder network for performing segmentation, in accordance with one or more embodiments. While framework 700 of FIG. 7 is shown for training the encoder network and decoder network for performing segmentation, it should be understood that framework 700 may be performed for training the encoder network and decoder network for performing any other suitable medical imaging analysis task. Framework 700 is performed during a prior offline or training stage. Once trained, the trained encoder network and the trained decoder network are applied during an online or inference stage, e.g., to perform steps 104 and 106 of FIG. 1 or step 604 and 606 of FIG. 6.

Encoder network 704 is trained to encode training image 702 into embeddings. Training image 702 is of a temporal sequence of training medical images. The embeddings for training image 702 are stored in memory bank 708, along with embeddings for one or more other training images of the temporal sequence of training medical images. Decoder network 708 is trained to decode embeddings for training image 702 and embeddings for the one or more other training images stored in memory bank 706 to generate segmentation mask 710.

As shown in framework 700, encoder network 704 and decoder network 708 are trained via loss backpropagation 718 according to loss function 716, which is based on segmentation loss 712 and temporal consistency loss 714. Temporal consistency loss 714 ensures temporal image-to-image consistency and progressive consistency. Motion consistency is a result of frame-to-frame and progressive consistency. Temporal consistency loss 714 measures the consistency between images and can be parameterized to also measure consistency between images within larger time intervals. The parameterization is task dependent and proportional with the total number of images used as input.

FIG. 8 shows a method 800 for performing a medical imaging analysis task with temporal consistency using CNN and transformer-based networks, in accordance with one or more embodiments. The steps of method 800 may be performed by one or more suitable computing devices, such as, e.g., computer 1502 of FIG. 15.

At step 802 of FIG. 8, a plurality of input medical images of a temporal sequence of medical images is received. Step 802 of FIG. 8 corresponds with step 102 of FIG. 1.

At step 804 of FIG. 8, temporal relationships are generated for the embeddings. The temporal relationships are defined based on temporal relationships between the input medical images in the temporal sequence of medical images.

At step 806 of FIG. 8, the embeddings are encoded with the temporal relationships using a transformer-based encoder network. The embeddings are encoded with the temporal relationships by, for example, conditioning the embeddings for a respective image of the plurality of input medical images at a time step t with one or more of the plurality of input medical images at a prior time step (e.g., t−1, t−2, etc.). In one embodiment, the transformer-based encoder network is a general pretrained CNN based encoder network. The transformer-based encoder network receives as input the embeddings and the temporal relationships and generates as output the encoded embeddings.

At step 808 of FIG. 8, a medical imaging analysis task is performed based on the encoded embeddings (encoded with the temporal relationships at step 806) using a transformer-based decoder network. Step 808 of FIG. 8 corresponds to step 106 of FIG. 1. The medical imaging analysis task may comprise detection, classification, segmentation, or any other suitable medical imaging analysis task. The transformer-based decoder network receives as input the encoded embeddings and generates as output results of the medical imaging analysis task. The transformer-based encoder-decoder architecture enables task specialization for performing the medical imaging analysis task, while also facilitating processing of larger contexts (e.g., to use data from other images).

At step 810 of FIG. 8, results of the medical imaging analysis task are output. Step 810 of FIG. 8 corresponds to step 108 of FIG. 1.

Figure 9:
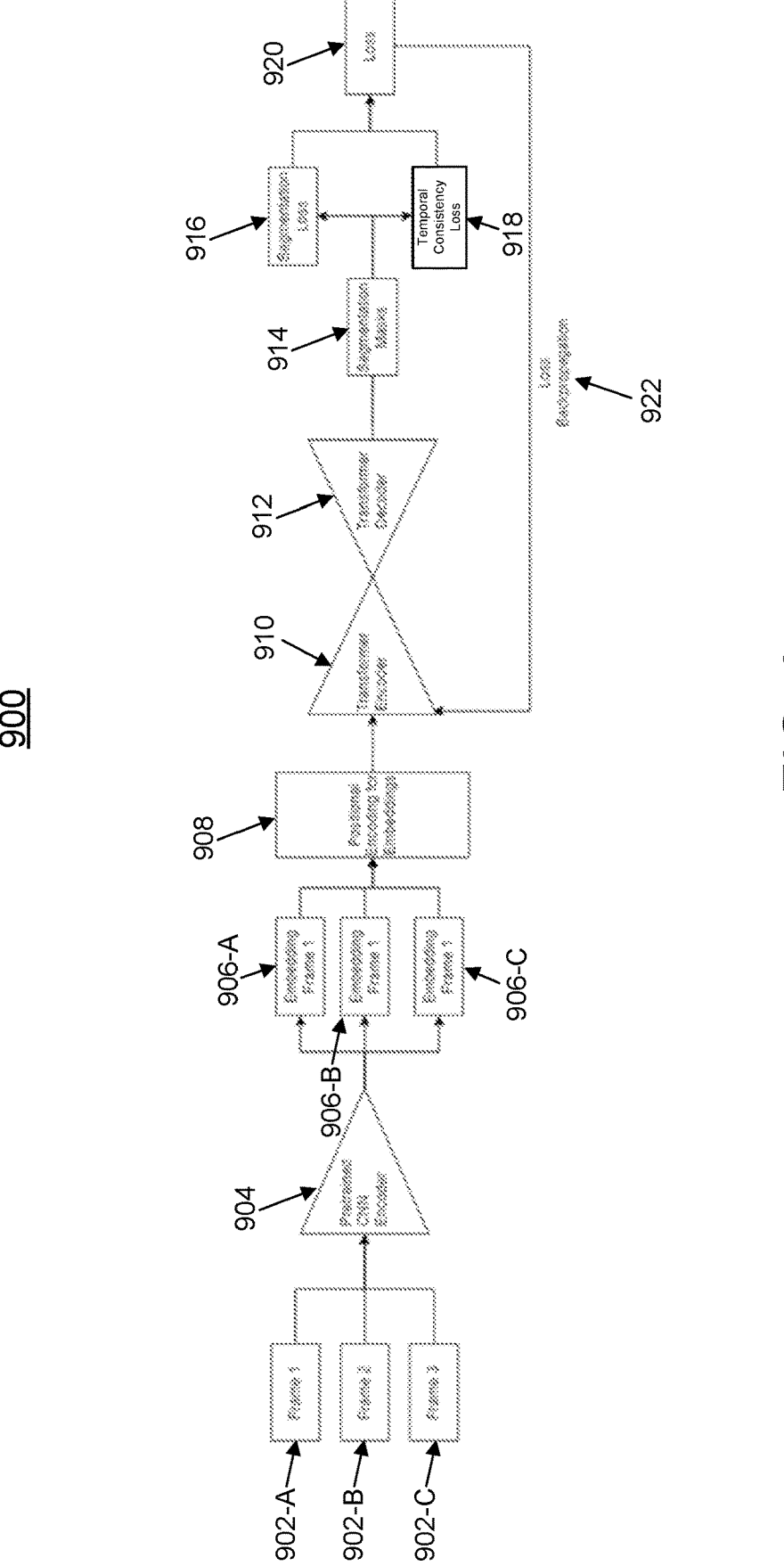
FIG. 9 shows a framework training transformer-based encoder and decoder networks for performing segmentation, in accordance with one or more embodiments.

The transformer-based encoder and decoder networks are trained during a prior offline or training stage, e.g., according to framework 900 of FIG. 9. Once trained, the trained encoder network and the trained decoder network are applied during an online or inference stage, e.g., to perform step 106 of FIG. 1 or steps 804 and 808 of FIG. 8.

FIG. 9 shows a framework 900 training transformer-based encoder and decoder networks for performing segmentation, in accordance with one or more embodiments. While framework 900 of FIG. 9 is shown for training the transformer-based encoder and decoder networks for performing segmentation, it should be understood that framework 900 may be performed for training the transformer-based encoder and decoder networks for performing any other suitable medical imaging analysis task. Framework 900 is performed during a prior offline or training stage. Once trained, the trained transformer-based encoder and decoder networks are applied during an online or inference stage, e.g., to perform step 106 of FIG. 1 or steps 804 and 808 of FIG. 8.

Pretrained CNN based encoder network 904 is trained to encode training images or frames 902-A, 902-B, and 902-C (collectively referred to as training images 902) of a temporal sequence of training images into respective embeddings 906-A, 906-B, and 906-C (collectively referred to as embeddings 906). Positional encoding for embeddings module 908 generates temporal relationships for embeddings 906. The temporal relationships are generated, for example, based on the temporal relationships between training images 902 in the temporal sequence of training images. Transformer-based encoder network 910 is trained to encode the embeddings 906 with the temporal relationships into encoded embeddings and transformer-based decoder network 912 is trained to decode the encoded embeddings to generate segmentation masks 914. Similar to framework 700 of FIG. 7, encoder network 910 and decoder network 912 are trained via loss backpropagation 922 according to loss function 920, which is based on segmentation loss 916 and temporal consistency loss 918.

FIG. 10 shows a method 1000 for performing a medical imaging analysis task with temporal consistency using transformer-based networks, in accordance with one or more embodiments. The steps of method 1000 may be performed by one or more suitable computing devices, such as, e.g., computer 1502 of FIG. 15.

At step 1002 of FIG. 10, a plurality of input medical images of a temporal sequence of medical images is received. Step 1002 of FIG. 10 corresponds with step 102 of FIG. 1.

At step 1004 of FIG. 10, patches are extracted from the plurality of input medical images. The patches may be overlapping or non-overlapping, and may be of a predetermined size.

At step 1006 of FIG. 10, temporal relationships are generated for the patches. The temporal relationships are defined based on temporal relationships between the input medical images, from which the patches were extracted, in the temporal sequence of medical images.

At step 1008 of FIG. 10, the patches are encoded, with the temporal relationships, into the embeddings using a transformer-based encoder network. Step 1008 of FIG. 10 corresponds to step 104 of FIG. 1. The transformer-based encoder network receives as input the patches and the temporal relationships and generates as output the embeddings.

In one embodiment, the patches are additionally or alternatively encoded into the embeddings based on one or more of spatial, temporal, anatomical, cardiac phase, and angulation information extracted from the one or more input medical images. The spatial information may comprise, for example, x and y coordinate of a patch. The temporal information may comprise, for example, a position of the image (frame) in the temporal sequence (e.g., index or acquisition time of a frame in an angio sequence). The cardia phase information may comprise, for example, a temporal position relative to the cardiac cycle (e.g., diastole phase, systole phase, end diastole phase, end systole phase, 60% phase) or a branch index/name or any priors based on vasculature. The angulation information may comprise, for example, C-arm angulation from which the image was acquired (e.g., LAO (left anterior oblique) 40 degrees and Caudal 30 degrees).

At step 1010 of FIG. 10, a medical imaging analysis task is performed based on the embeddings using a transformer-based decoder network. Step 1010 of FIG. 10 corresponds to step 106 of FIG. 1. The medical imaging analysis task may comprise detection, classification, segmentation, or any other suitable medical imaging analysis task. The transformer-based decoder network receives as input the embeddings and generates as output results of the medical imaging analysis task.

At step 1012 of FIG. 10, results of the medical imaging analysis task are output. Step 1012 of FIG. 10 corresponds to step 108 of FIG. 1.

In contrast to method 800 of FIG. 8, the transformer-based encoder and decoder networks utilized in method 1000 of FIG. 10 learns to encode the image patches with temporal relationships into embeddings while also specializing for the medical imaging analysis task. Therefore, the transformer-based encoder and decoder networks are more sensitive to the size of the training data set. To ease the impact of the training data set size, a large-scale pretrained transformer network can be used as a start.

Figure 11:
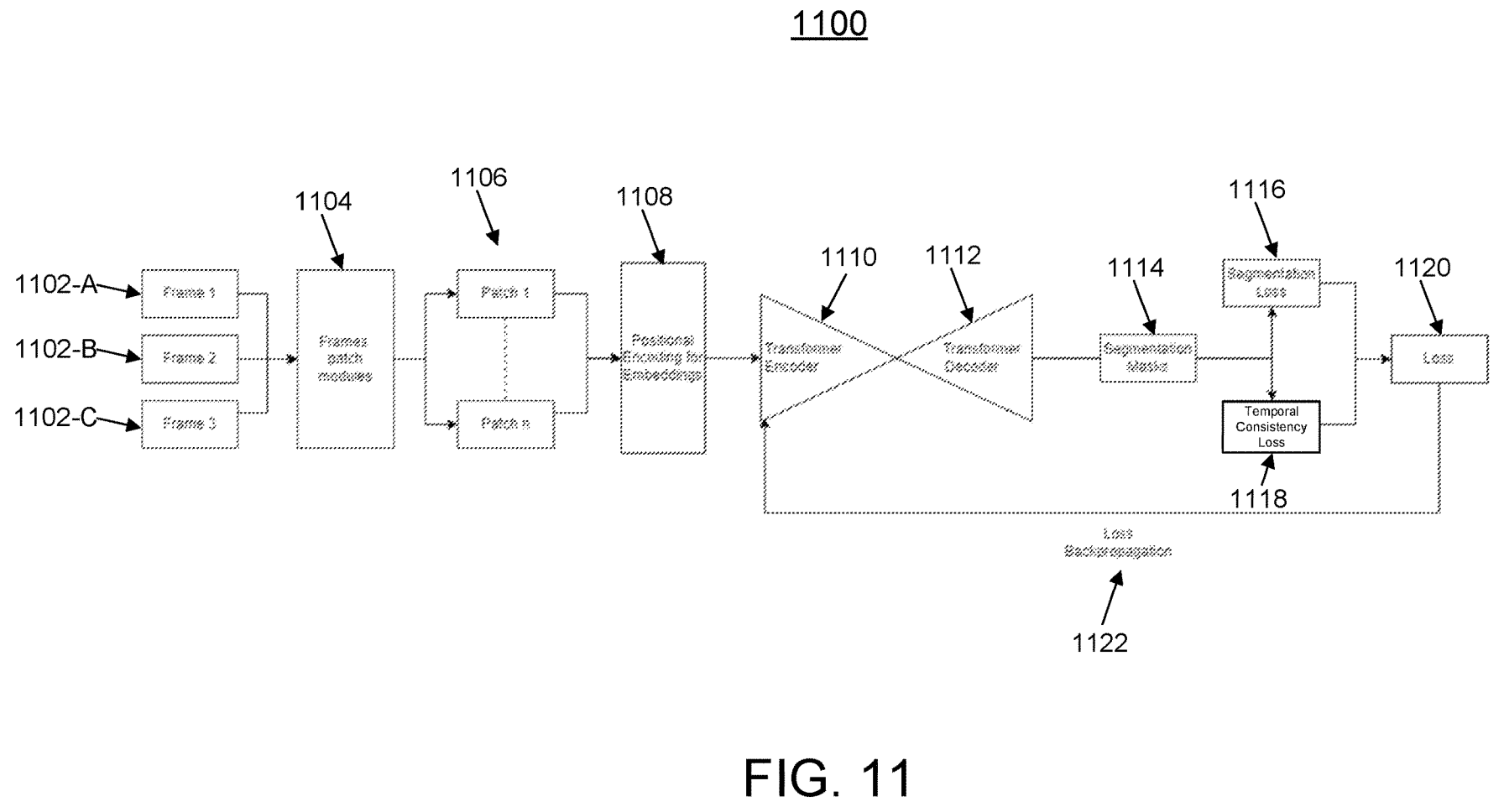

The transformer-based encoder and decoder networks are trained during a prior offline or training stage, e.g., according to framework 1100 of FIG. 11. Once trained, the trained transformer-based encoder and decoder networks are applied during an online or inference stage, e.g., to perform step 106 of FIG. 1 or steps 1008 and 1010 of FIG. 10.

FIG. 11 shows a framework 1100 training transformer-based encoder and decoder networks for performing segmentation, in accordance with one or more embodiments. While framework 1100 of FIG. 11 is shown for training the transformer-based encoder and decoder networks for performing segmentation, it should be understood that framework 1100 may be performed for training the transformer-based encoder and decoder networks for performing any other suitable medical imaging analysis task. Framework 1100 is performed during a prior offline or training stage. Once trained, the trained encoder network and the trained decoder network are applied during an online or inference stage, e.g., to perform step 106 of FIG. 1 or steps 1008 and 1010 of FIG. 10.

Frames patch modules 1104 extracts patches 1106 from training images or frames 1102-A, 1102-B, and 1102-C (collectively referred to as training images 1102) of a temporal sequence of training images. Positional encoding for embeddings module 1108 generates temporal relationships for patches 1106. Transformer-based encoder network 1110 is trained to encode patches 1106, with the temporal relationships, into encoded embeddings. The temporal relationships are based on the temporal relationships between training images 1106 in the temporal sequence of training images. Transformer-based decoder network 1112 is trained to decode the encoded embeddings to generate segmentation masks 1114. Similar to framework 700 of FIG. 7, encoder network 1110 and decoder network 1112 are trained via loss backpropagation 1122 according to loss function 1120, which is based on segmentation loss 1116 and temporal consistency loss 1118.

Figure 12:
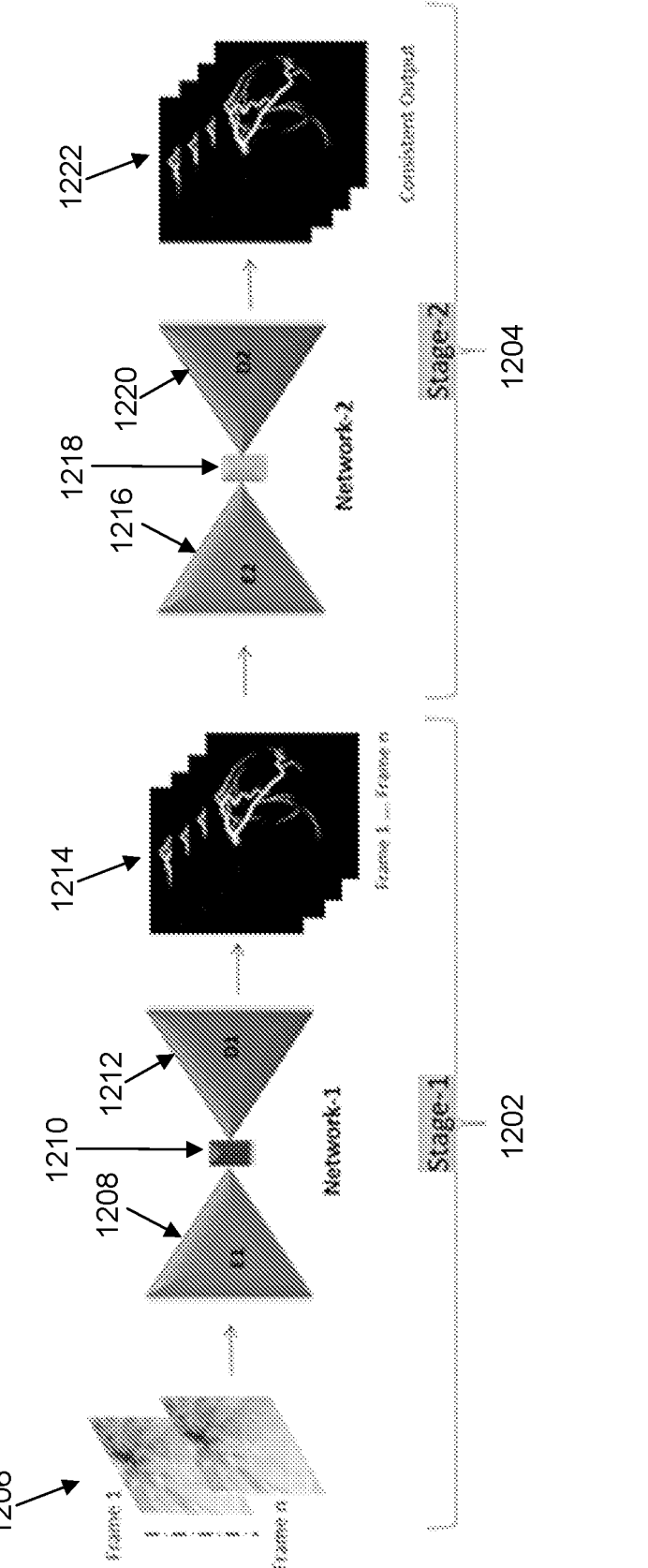
FIG. 12 shows a workflow for a two-stage approach for generating temporally consistent results of a medical imaging analysis task, in accordance with one or more embodiments.

FIG. 12 shows a workflow 1200 for a two-stage approach for generating temporally consistent results of a medical imaging analysis task, in accordance with one or more embodiments. Workflow 1200 comprises stage 1 1202 and stage 2 1204. In stage 1 1202, encoder network 1208 receives a plurality of input medical images or frames 1206 of a temporal sequence of medical images as input and encodes the plurality of input medical images 1206 into embeddings 1210. Decoder network 1212 decodes embeddings 1210 to generate results 1210 of a medical imaging analysis task (e.g., segmentation). Encoder network 1208/ decoder network 1212 are focused on producing highly accurate results of the medical imaging analysis task for the entire temporal sequence. In stage 2 1204, encoder network 1216 receives results 1214 as input and encodes results 1214 into embeddings 1218. Decoder network 1220 decodes embeddings 1218 to generate results final results 1214 of the medical imaging analysis task that are temporally consistent. Encoder network 1208/decoder network 1212 may be trained using cross entropy or dice loss, while encoder network 1216/decoder network 1220 may be trained with a consistency loss. Advantageously, the two-stage approach of workflow 1200 enables the use of either results 1214 or final results 1222 depending on the application. Encoder network 1208/decoder network 1212 and/or encoder network 1216/ decoder network 1220 can be implemented as a CNN, a transformer, or a combination thereof.

In one embodiment, the medical imaging analysis tasks may comprise various classification, detection, and segmentation tasks, such as, e.g., temporally consistent segmentation of the coronary lumen, temporally consistent detection and segmentation of devices (e.g., catheter tip, guidewire, or any other interventional device), temporally consistent detection of coronary stenosis, temporally consistent detection of heatmaps (e.g., segment labelling, branch overlaps, foreshortening), or temporally consistent detection of landmarks (e.g., coronary ostia).

In one embodiment, the temporally consistent coronary lumen extracted in accordance with embodiments described herein can be used as a dynamic vessel roadmap overlaid on a live fluoroscopy to aid an interventional cardiologist (or any other user) to safely navigate devices under fluoroscopy guidance (without injecting additional contrast). Embodiments described herein results in temporally consistent vessel tree overlay and avoids the problem of "flickering vessels" (the sudden appearance/disappearance of a small side branch) that is often reported with conventional approaches that are not temporally consistent.

In one embodiment, the same coronary lumen can be used for robotic PCI (percutaneous coronary intervention) navigation, where the underlying lumen map together with a temporally consistent device tracking (e.g., catheter tracking) can be used to provide automatic feedback for detected events, such as, e.g., guidewire entering a side-branch, stent reaching the pre-planned landing zone in a stenosis region, guidewire causing a vessel dissection, etc.

For complex PCI cases such as CTO (coronary total occlusion), embodiments described herein provides a higher quality lumen extraction since there are several collateral vessels which have retrograde contrast filling, resulting in inconsistent visual appearance across the cardiac cycle.

Embodiments described herein are described with respect to the claimed systems as well as with respect to the claimed methods. Features, advantages or alternative embodiments herein can be assigned to the other claimed objects and vice versa. In other words, claims for the systems can be improved with features described or claimed in the context of the methods. In this case, the functional features of the method are embodied by objective units of the providing system.

Furthermore, certain embodiments described herein are described with respect to methods and systems utilizing trained machine learning based models, as well as with respect to methods and systems for training machine learning based models. Features, advantages or alternative embodiments herein can be assigned to the other claimed objects and vice versa. In other words, claims for methods and systems for training a machine learning based model can be improved with features described or claimed in context of the methods and systems for utilizing a trained machine learning based model, and vice versa.

In particular, the trained machine learning based models applied in embodiments described herein can be adapted by the methods and systems for training the machine learning based models. Furthermore, the input data of the trained machine learning based model can comprise advantageous features and embodiments of the training input data, and vice versa. Furthermore, the output data of the trained machine learning based model can comprise advantageous features and embodiments of the output training data, and vice versa.

In general, a trained machine learning based model mimics cognitive functions that humans associate with other human minds. In particular, by training based on training data, the trained machine learning based model is able to adapt to new circumstances and to detect and extrapolate patterns.

In general, parameters of a machine learning based model can be adapted by means of training. In particular, supervised training, semi-supervised training, unsupervised training, reinforcement learning and/or active learning can be used. Furthermore, representation learning (an alternative term is "feature learning") can be used. In particular, the parameters of the trained machine learning based model can be adapted iteratively by several steps of training.

In particular, a trained machine learning based model can comprise a neural network, a support vector machine, a decision tree, and/or a Bayesian network, and/or the trained machine learning based model can be based on k-means clustering, Q-learning, genetic algorithms, and/or association rules. In particular, a neural network can be a deep neural network, a convolutional neural network, or a convolutional deep neural network. Furthermore, a neural network can be an adversarial network, a deep adversarial network and/or a generative adversarial network.

Figure 13:
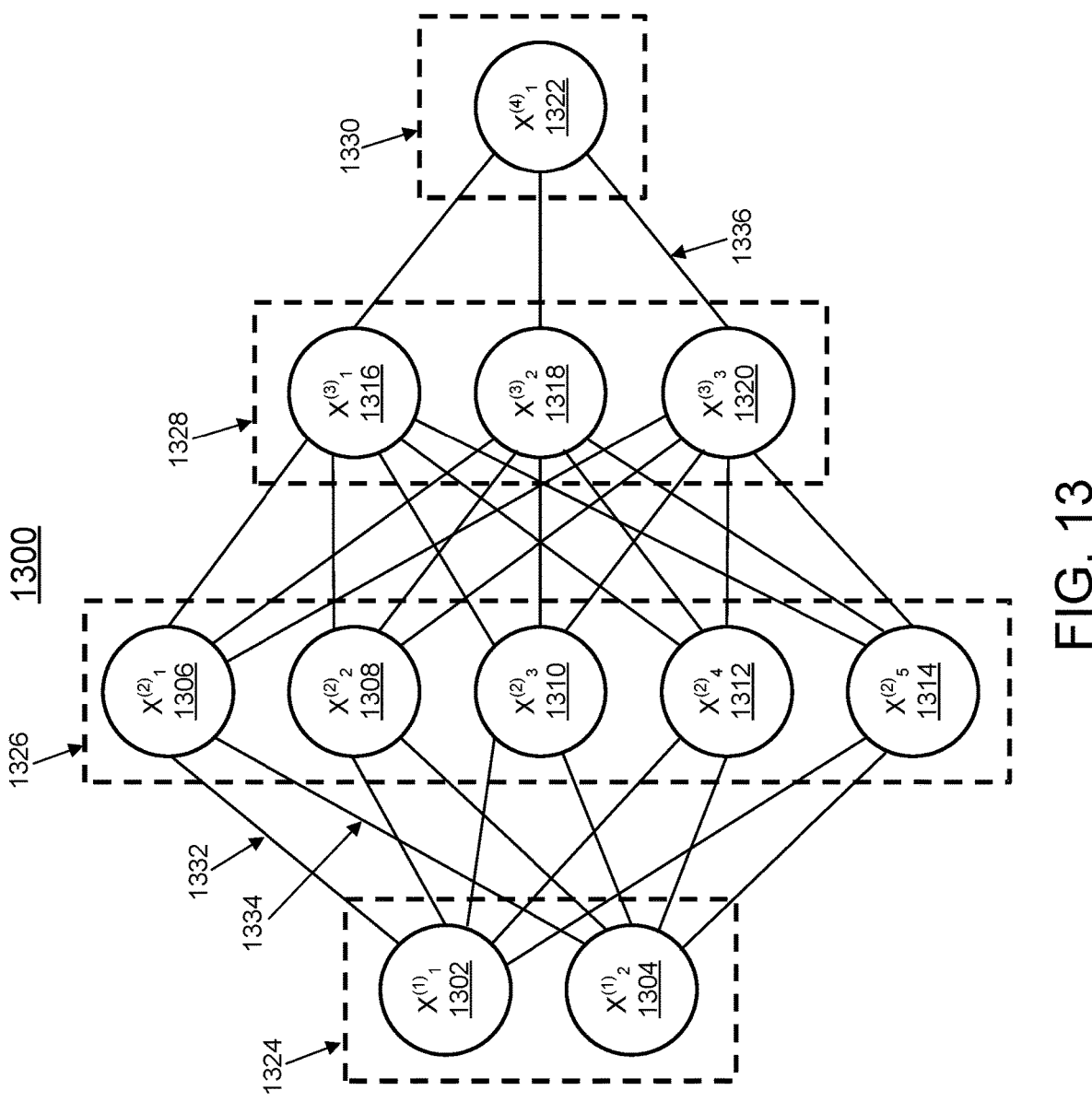
FIG. 13 shows an exemplary artificial neural network that may be used to implement one or more embodiments.

FIG. 13 shows an embodiment of an artificial neural network 1300, in accordance with one or more embodiments. Alternative terms for "artificial neural network" are "neural network", "artificial neural net" or "neural net". Machine learning networks described herein, such as, e.g., the machine learning based networks utilized in steps 104 and 106 of FIG. 1, the machine learning based networks utilized in steps 204 and 206 of FIG. 2, encoder network 304 of FIG. 3, vision transformer encoder 406 and decoder 414 of FIG. 4, pretrained vision transformer encoder 506 of FIG. 5, the machine learning based networks utilized in steps 604 and 606 of FIG. 6, CNN based encoder network 704, memory bank 706 and CNN based decoder 708 of FIG. 7, the machine learning based networks utilized in steps 804 and 808 of FIG. 8, pretrained CNN based encoder network 904, transformer-based encoder 910, and transformer-based decoder 912 of FIG. 9, the machine learning based networks utilized in steps 1008 and 1010 of FIG. 10, transformer-based encoder network 1110 and transformer-based decoder network 1112 of FIG. 11, and encoder network 1208, decoder network 1212, encoder network 1216, and decoder network 1220 of FIG. 12, may be implemented using artificial neural network 1300.

The artificial neural network 1300 shown in FIG. 13 is a feedforward neural network comprising nodes 1302-1322 and edges 1332, 1334, . . . , 1336, wherein each edge 1332, 1334, . . . , 1336 is a directed connection from a first node 1302-1322 to a second node 1302-1322. In general, the first node 1302-1322 and the second node 1302-1322 are different nodes 1302-1322, it is also possible that the first node 1302-1322 and the second node 1302-1322 are identical. For example, in FIG. 13, the edge 1332 is a directed connection from the node 1302 to the node 1306, and the edge 1334 is a directed connection from the node 1304 to the node 1306. An edge 1332, 1334, . . . , 1336 from a first node 1302-1322 to a second node 1302-1322 is also denoted as "ingoing edge" for the second node 1302-1322 and as "outgoing edge" for the first node 1302-1322.

In this embodiment, the nodes 1302-1322 of the artificial neural network 1300 can be arranged in layers 1324-1330, wherein the layers can comprise an intrinsic order introduced by the edges 1332, 1334, . . . , 1336 between the nodes 1302-1322. In particular, edges 1332, 1334, . . . , 1336 can exist only between neighboring layers of nodes. In the embodiment shown in FIG. 13, there is an input layer 1324 comprising only nodes 1302 and 1304 without an incoming edge, an output layer 1330 comprising only node 1322 without outgoing edges, and hidden layers 1326, 1328 in-between the input layer 1324 and the output layer 1330. In general, the number of hidden layers 1326, 1328 can be chosen arbitrarily. The number of nodes 1302 and 1304 within the input layer 1324 usually relates to the number of input values of the neural network 1300, and the number of nodes 1322 within the output layer 1330 usually relates to the number of output values of the neural network 1300.

In particular, a (real) number can be assigned as a value to every node 1302-1322 of the neural network 1300. Here, $x^{(n)}_i$ denotes the value of the i-th node 1302-1322 of the n-th layer 1324-1330. The values of the nodes 1302-1322 of the input layer 1324 are equivalent to the input values of the neural network 1300, the value of the node 1322 of the output layer 1330 is equivalent to the output value of the neural network 1300. Furthermore, each edge 1332, 1334, . . . , 1336 can comprise a weight being a real number, in particular, the weight is a real number within the interval [−1, 1] or within the interval [0, 1]. Here, $w^{(m,n)}_{i,j}$ denotes the weight of the edge between the i-th node 1302-1322 of the m-th layer 1324-1330 and the j-th node 1302-1322 of the n-th layer 1324-1330. Furthermore, the abbreviation $w^{(n)}_{i,j}$ is defined for the weight $w^{(n,n+1)}_{i,j}$.

In particular, to calculate the output values of the neural network 1300, the input values are propagated through the neural network. In particular, the values of the nodes 1302-1322 of the (n+1)-th layer 1324-1330 can be calculated based on the values of the nodes 1302-1322 of the n-th layer 1324-1330 by $$x_j^{(n+1)}=f(\Sigma_i x_i^{(n)}\cdot w_{i,j}^{(n)}).$$

Herein, the function f is a transfer function (another term is "activation function"). Known transfer functions are step functions, sigmoid function (e.g. the logistic function, the generalized logistic function, the hyperbolic tangent, the Arctangent function, the error function, the smoothstep function) or rectifier functions. The transfer function is mainly used for normalization purposes.

In particular, the values are propagated layer-wise through the neural network, wherein values of the input layer 1324 are given by the input of the neural network 1300, wherein values of the first hidden layer 1326 can be calculated based on the values of the input layer 1324 of the neural network, wherein values of the second hidden layer 1328 can be calculated based in the values of the first hidden layer 1326, etc.

In order to set the values $w^{(m,n)}_{i,j}$ for the edges, the neural network 1300 has to be trained using training data. In particular, training data comprises training input data and training output data (denoted as $t_i$). For a training step, the neural network 1300 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 1300 (backpropagation algorithm). In particular, the weights are changed according to $$w'^{(n)}_{i,j}=w_{i,j}^{(n)}-\gamma\cdot\delta_j^{(n)}\cdot x_i^{(n)}$$

wherein γ is a learning rate, and the numbers $\delta^{(n)}_j$ can be recursively calculated as $$\delta_j^{(n)}=(\Sigma_k\delta_k^{(n+1)}\cdot w_{j,k}^{(n+1)})\cdot f'(\Sigma_i x_i^{(n)}\cdot w_{i,j}^{(n)})$$

based on $\delta^{(n+1)}_j$, if the (n+1)-th layer is not the output layer, and $$\delta_j^{(n)}=(x_k^{(n+1)}-t_j^{(n+1)})\cdot f'(\Sigma_i x_i^{(n)}\cdot w_{i,j}^{(n)})$$

if the (n+1)-th layer is the output layer 1330, wherein f' is the first derivative of the activation function, and $y^{(n+1)}_j$ is the comparison training value for the j-th node of the output layer 1330.

Figure 14:
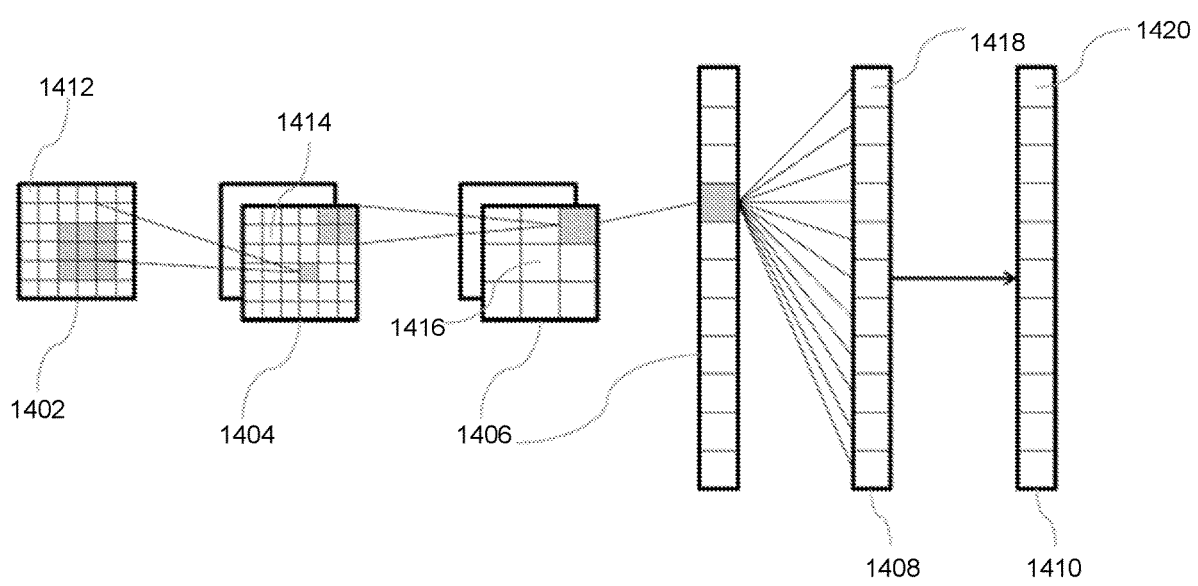
FIG. 14 shows a convolutional neural network that may be used to implement one or more embodiments.

FIG. 14 shows a convolutional neural network 1400, in accordance with one or more embodiments. Machine learning networks described herein, such as, e.g., the machine learning based networks utilized in steps 104 and 106 of FIG. 1, the machine learning based networks utilized in steps 204 and 206 of FIG. 2, encoder network 304 of FIG. 3, vision transformer encoder 406 and decoder 414 of FIG. 4, pretrained vision transformer encoder 506 of FIG. 5, the machine learning based networks utilized in steps 604 and 606 of FIG. 6, CNN based encoder network 704, memory bank 706 and CNN based decoder 708 of FIG. 7, the machine learning based networks utilized in steps 804 and 808 of FIG. 8, pretrained CNN based encoder network 904, transformer-based encoder 910, and transformer-based decoder 912 of FIG. 9, the machine learning based networks utilized in steps 1008 and 1010 of FIG. 10, transformer-based encoder network 1110 and transformer-based decoder network 1112 of FIG. 11, and encoder network 1208, decoder network 1212, encoder network 1216, and decoder network 1220 of FIG. 12, may be implemented using convolutional neural network 1400.

In the embodiment shown in FIG. 14, the convolutional neural network comprises 1400 an input layer 1402, a convolutional layer 1404, a pooling layer 1406, a fully connected layer 1408, and an output layer 1410. Alternatively, the convolutional neural network 1400 can comprise several convolutional layers 1404, several pooling layers 1406, and several fully connected layers 1408, as well as other types of layers. The order of the layers can be chosen arbitrarily, usually fully connected layers 1408 are used as the last layers before the output layer 1410.

In particular, within a convolutional neural network 1400, the nodes 1412-1420 of one layer 1402-1410 can be considered to be arranged as a d-dimensional matrix or as a d-dimensional image. In particular, in the two-dimensional case the value of the node 1412-1420 indexed with i and j in the n-th layer 1402-1410 can be denoted as $x^{(n)}_{[i,j]}$. However, the arrangement of the nodes 1412-1420 of one layer 1402-1410 does not have an effect on the calculations executed within the convolutional neural network 1400 as such, since these are given solely by the structure and the weights of the edges.

In particular, a convolutional layer 1404 is characterized by the structure and the weights of the incoming edges forming a convolution operation based on a certain number of kernels. In particular, the structure and the weights of the incoming edges are chosen such that the values $x^{(n)}_k$ of the nodes 1414 of the convolutional layer 1404 are calculated as a convolution $x^{(n)}_k = K_k * x^{(n-1)}$ based on the values $x^{(n-1)}$ of the nodes 1412 of the preceding layer 1402, where the convolution * is defined in the two-dimensional case as $$x^{(n)}_k[i,j]=(K_k*x^{(n-1)})[i,j]=\Sigma_i\Sigma_j K_k[i',j']\cdot x^{(n-1)}[i-i',j-j'].$$

Here the k-th kernel $K_k$ is a d-dimensional matrix (in this embodiment a two-dimensional matrix), which is usually small compared to the number of nodes 1412-1418 (e.g. a 3×3 matrix, or a 5×5 matrix). In particular, this implies that the weights of the incoming edges are not independent, but chosen such that they produce said convolution equation. In particular, for a kernel being a 3×3 matrix, there are only 9 independent weights (each entry of the kernel matrix corresponding to one independent weight), irrespectively of the number of nodes 1412-1420 in the respective layer 1402-1410. In particular, for a convolutional layer 1404, the number of nodes 1414 in the convolutional layer is equivalent to the number of nodes 1412 in the preceding layer 1402 multiplied with the number of kernels.

If the nodes 1412 of the preceding layer 1402 are arranged as a d-dimensional matrix, using a plurality of kernels can be interpreted as adding a further dimension (denoted as "depth" dimension), so that the nodes 1414 of the convolutional layer 1404 are arranged as a (d+1)-dimensional matrix. If the nodes 1412 of the preceding layer 1402 are already arranged as a (d+1)-dimensional matrix comprising a depth dimension, using a plurality of kernels can be interpreted as expanding along the depth dimension, so that the nodes 1414 of the convolutional layer 1404 are arranged also as a (d+1)-dimensional matrix, wherein the size of the (d+1)-dimensional matrix with respect to the depth dimension is by a factor of the number of kernels larger than in the preceding layer 1402.

The advantage of using convolutional layers 1404 is that spatially local correlation of the input data can exploited by enforcing a local connectivity pattern between nodes of adjacent layers, in particular by each node being connected to only a small region of the nodes of the preceding layer.

In embodiment shown in FIG. 14, the input layer 1402 comprises 36 nodes 1412, arranged as a two-dimensional 6×6 matrix. The convolutional layer 1404 comprises 72 nodes 1414, arranged as two two-dimensional 6×6 matrices, each of the two matrices being the result of a convolution of the values of the input layer with a kernel. Equivalently, the nodes 1414 of the convolutional layer 1404 can be interpreted as arranges as a three-dimensional 6×6×2 matrix, wherein the last dimension is the depth dimension.

A pooling layer 1406 can be characterized by the structure and the weights of the incoming edges and the activation function of its nodes 1416 forming a pooling operation based on a non-linear pooling function f. For example, in the two dimensional case the values $x^{(n)}$ of the nodes 1416 of the pooling layer 1406 can be calculated based on the values $x^{(n-1)}$ of the nodes 1414 of the preceding layer 1404 as $$x^{(n)}[i,j]=f(x^{(n-1)}[id_1,jd_2], \ldots ,x^{(n-1)}[id_1+d_1-1,jd_2+d_2-1])$$

In other words, by using a pooling layer 1406, the number of nodes 1414, 1416 can be reduced, by replacing a number $d_1 \cdot d_2$ of neighboring nodes 1414 in the preceding layer 1404 with a single node 1416 being calculated as a function of the values of said number of neighboring nodes in the pooling layer. In particular, the pooling function f can be the max-function, the average or the L2-Norm. In particular, for a pooling layer 1406 the weights of the incoming edges are fixed and are not modified by training.

The advantage of using a pooling layer 1406 is that the number of nodes 1414, 1416 and the number of parameters is reduced. This leads to the amount of computation in the network being reduced and to a control of overfitting.

In the embodiment shown in FIG. 14, the pooling layer 1406 is a max-pooling, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

A fully-connected layer 1408 can be characterized by the fact that a majority, in particular, all edges between nodes 1416 of the previous layer 1406 and the nodes 1418 of the fully-connected layer 1408 are present, and wherein the weight of each of the edges can be adjusted individually.

In this embodiment, the nodes 1416 of the preceding layer 1406 of the fully-connected layer 1408 are displayed both as two-dimensional matrices, and additionally as non-related nodes (indicated as a line of nodes, wherein the number of nodes was reduced for a better presentability). In this embodiment, the number of nodes 1418 in the fully connected layer 1408 is equal to the number of nodes 1416 in the preceding layer 1406. Alternatively, the number of nodes 1416, 1418 can differ.

Furthermore, in this embodiment, the values of the nodes 1420 of the output layer 1410 are determined by applying the Softmax function onto the values of the nodes 1418 of the preceding layer 1408. By applying the Softmax function, the sum the values of all nodes 1420 of the output layer 1410 is 1, and all values of all nodes 1420 of the output layer are real numbers between 0 and 1.

A convolutional neural network 1400 can also comprise a ReLU (rectified linear units) layer or activation layers with non-linear transfer functions. In particular, the number of nodes and the structure of the nodes contained in a ReLU layer is equivalent to the number of nodes and the structure of the nodes contained in the preceding layer. In particular, the value of each node in the ReLU layer is calculated by applying a rectifying function to the value of the corresponding node of the preceding layer.

The input and output of different convolutional neural network blocks can be wired using summation (residual/dense neural networks), element-wise multiplication (attention) or other differentiable operators. Therefore, the convolutional neural network architecture can be nested rather than being sequential if the whole pipeline is differentiable.

In particular, convolutional neural networks 1400 can be trained based on the backpropagation algorithm. For preventing overfitting, methods of regularization can be used, e.g. dropout of nodes 1412-1420, stochastic pooling, use of artificial data, weight decay based on the L1 or the L2 norm, or max norm constraints. Different loss functions can be combined for training the same neural network to reflect the joint training objectives. A subset of the neural network parameters can be excluded from optimization to retain the weights pretrained on another data sets.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIGS. 1-12. Certain steps or functions of the methods and workflows described herein, including one or more of the steps or functions of FIGS. 1-12, may be performed by a server or by another processor in a network-based cloud-computing system. Certain steps or functions of the methods and workflows described herein, including one or more of the steps of FIGS. 1-12, may be performed by a client computer in a network-based cloud computing system. The steps or functions of the methods and workflows described herein, including one or more of the steps of FIGS. 1-12, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIGS. 1-12, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 15:
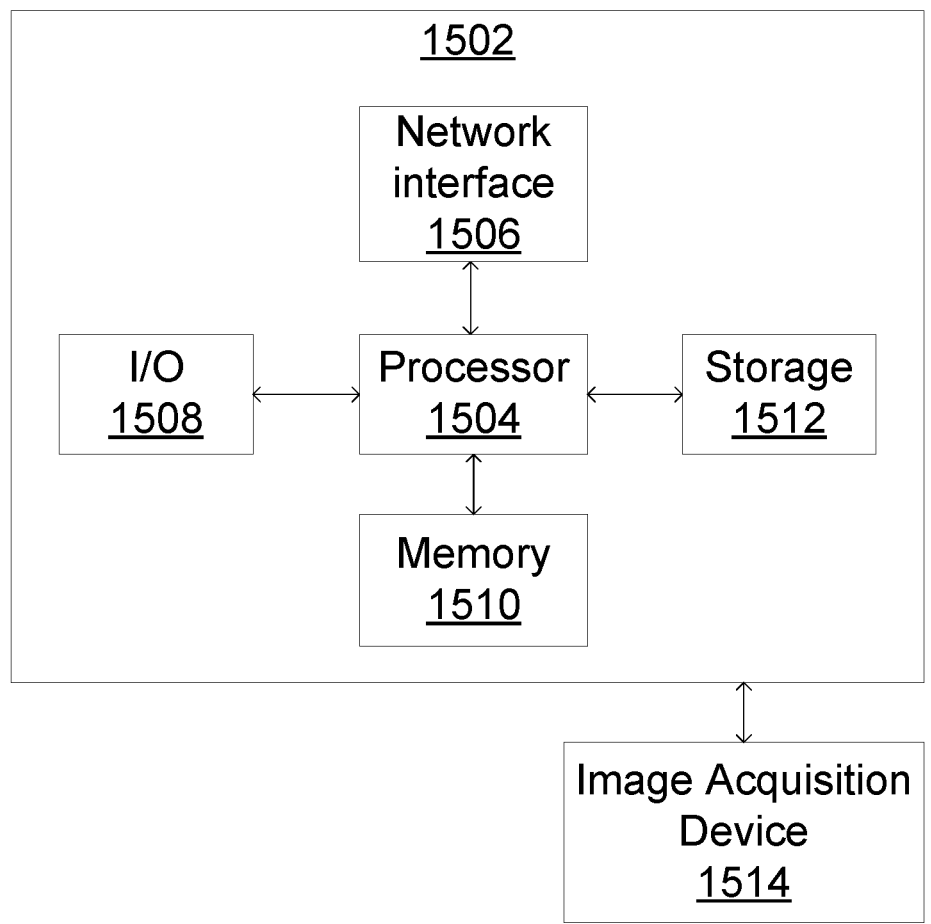
FIG. 15 shows a high-level block diagram of a computer that may be used to implement one or more embodiments.

A high-level block diagram of an example computer 1502 that may be used to implement systems, apparatus, and methods described herein is depicted in FIG. 15. Computer 1502 includes a processor 1504 operatively coupled to a data storage device 1512 and a memory 1510. Processor 1504 controls the overall operation of computer 1502 by executing computer program instructions that define such operations. The computer program instructions may be stored in data storage device 1512, or other computer readable medium, and loaded into memory 1510 when execution of the computer program instructions is desired. Thus, the method and workflow steps or functions of FIGS. 1-12 can be defined by the computer program instructions stored in memory 1510 and/or data storage device 1512 and controlled by processor 1504 executing the computer program instructions. For example, the computer program instructions can be implemented as computer executable code programmed by one skilled in the art to perform the method and workflow steps or functions of FIGS. 1-12. Accordingly, by executing the computer program instructions, the processor 1504 executes the method and workflow steps or functions of FIGS. 1-12. Computer 1502 may also include one or more network interfaces 1506 for communicating with other devices via a network. Computer 1502 may also include one or more input/output devices 1508 that enable user interaction with computer 1502 (e.g., display, keyboard, mouse, speakers, buttons, etc.).

Processor 1504 may include both general and special purpose microprocessors, and may be the sole processor or one of multiple processors of computer 1502. Processor 1504 may include one or more central processing units (CPUs), for example. Processor 1504, data storage device 1512, and/or memory 1510 may include, be supplemented by, or incorporated in, one or more application-specific integrated circuits (ASICs) and/or one or more field programmable gate arrays (FPGAs).

Data storage device 1512 and memory 1510 each include a tangible non-transitory computer readable storage medium. Data storage device 1512, and memory 1510, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 1508 may include peripherals, such as a printer, scanner, display screen, etc. For example, input/output devices 1508 may include a display device such as a cathode ray tube (CRT) or liquid crystal display (LCD) monitor for displaying information to the user, a keyboard, and a pointing device such as a mouse or a trackball by which the user can provide input to computer 1502.

An image acquisition device 1514 can be connected to the computer 1502 to input image data (e.g., medical images) to the computer 1502. It is possible to implement the image acquisition device 1514 and the computer 1502 as one device. It is also possible that the image acquisition device 1514 and the computer 1502 communicate wirelessly through a network. In a possible embodiment, the computer 1502 can be located remotely with respect to the image acquisition device 1514.

Any or all of the systems and apparatus discussed herein may be implemented using one or more computers such as computer 1502.

One skilled in the art will recognize that an implementation of an actual computer or computer system may have other structures and may contain other components as well, and that FIG. 15 is a high level representation of some of the components of such a computer for illustrative purposes.

Independent of the grammatical term usage, individuals with male, female or other gender identities are included within the term.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A computer-implemented method comprising:
    receiving a plurality of input medical images of a patient, the plurality of input medical images comprising a query image and one or more candidate images;
    encoding the plurality of input medical images into embeddings using a machine learning based encoder network;
    performing a medical imaging analysis task by determining at least one of the one or more candidate images as corresponding to the query image based on the embeddings using the machine learning based encoder network, wherein determining at least one of the one or more candidate images as corresponding to the query image based on the embeddings using the machine learning based encoder network comprises:
        ranking the embeddings for the one or more candidate images based on a similarity to the embeddings for the query image using the machine learning based encoder network; and
    outputting results of the medical imaging analysis task.

2. The computer-implemented method of claim 1, further comprising:
    extracting patches from the plurality of input medical images,
    wherein encoding the plurality of input medical images into embeddings using a machine learning based encoder network comprises:
        encoding the patches into the embeddings based on one or more of spatial, temporal, anatomical, cardiac phase, and angulation information extracted from the plurality of input medical images using a transformer-based encoder network.

3. The computer-implemented method of claim 1, wherein determining at least one of the one or more candidate images as corresponding to the query image based on the embeddings using the machine learning based encoder network further comprises:
    generating matching scores between the embeddings using the machine learning based encoder network.

4. The computer-implemented method of claim 1, wherein the plurality of input medical images comprises coronary angiography images of the patient.

5. A computer-implemented method comprising:
    receiving a plurality of input medical images of a temporal sequence of medical images of a patient;
    extracting patches from the plurality of input medical images;
    generating temporal relationships for the patches;
    encoding the plurality of input medical images into embeddings using a machine learning based encoder network, wherein encoding the plurality of input medical images into embeddings using a machine learning based encoder network comprises:
        encoding the patches, with the temporal relationships, into the embeddings using a transformer-based encoder network;
    performing a medical imaging analysis task based on the embeddings, wherein performing a medical imaging analysis task based on the embeddings comprises:
        performing the medical imaging analysis task based on the embeddings using a transformer-based decoder network; and
    outputting results of the medical imaging analysis task.

6. The computer-implemented method of claim 5, further comprising:
    extracting patches from the plurality of input medical images,
    wherein encoding the plurality of input medical images into embeddings using a machine learning based encoder network comprises:
        encoding the patches into the embeddings based on one or more of spatial, temporal, anatomical, cardiac phase, and angulation information extracted from the plurality of input medical images using a transformer-based encoder network.

7. The computer-implemented method of claim 5, wherein the plurality of input medical images comprises coronary angiography images of the patient.

8. An apparatus comprising:

means for receiving a plurality of input medical images of a temporal sequence of medical images of a patient;

means for extracting patches from the plurality of input medical images;

means for generating temporal relationships for the patches;

means for encoding the plurality of input medical images into embeddings using a machine learning based encoder network, wherein the means for encoding the plurality of input medical images into embeddings using a machine learning based encoder network comprises:

means for encoding the patches, with the temporal relationships, into the embeddings using a transformer-based encoder network;

means for performing a medical imaging analysis task based on the embeddings, wherein the means for performing a medical imaging analysis task based on the embeddings comprises:

means for performing the medical imaging analysis task based on the embeddings using a transformer-based decoder network; and means for outputting results of the medical imaging analysis task.

9. The apparatus of claim 8, further comprising:

means for extracting patches from the plurality of input medical images, wherein the means for encoding the plurality of input medical images into embeddings using a machine learning based encoder network comprises:

means for encoding the patches into the embeddings based on one or more of spatial, temporal, anatomical, cardiac phase, and angulation information extracted from the plurality of input medical images using a transformer-based encoder network.

10. The apparatus of claim 8, wherein the plurality of input medical images comprises coronary angiography images of the patient.

11. An apparatus comprising:

means for receiving a plurality of input medical images of a patient, the plurality of input medical images comprising a query image and one or more candidate images;

means for encoding the plurality of input medical images into embeddings using a machine learning based encoder network;

means for performing a medical imaging analysis task by determining at least one of the one or more candidate images as corresponding to the query image based on the embeddings using the machine learning based encoder network, wherein determining at least one of the one or more candidate images as corresponding to the query image based on the embeddings using the machine learning based encoder network comprises:

means for ranking the embeddings for the one or more candidate images based on a similarity to the embeddings for the query image using the machine learning based encoder network; and means for outputting results of the medical imaging analysis task.

12. The apparatus of claim 11, wherein determining at least one of the one or more candidate images as corresponding to the query image based on the embeddings using the machine learning based encoder network further comprises:

means for generating matching scores between the embeddings using the machine learning based encoder network.

13. The apparatus of claim 11, further comprising:

means for extracting patches from the plurality of input medical images, wherein the means for encoding the plurality of input medical images into embeddings using a machine learning based encoder network comprises:

means for encoding the patches into the embeddings based on one or more of spatial, temporal, anatomical, cardiac phase, and angulation information extracted from the plurality of input medical images using a transformer-based encoder network.

14. The apparatus of claim 11, wherein the plurality of input medical images comprises coronary angiography images of the patient.

15. A non-transitory computer readable medium storing computer program instructions, the computer program instructions when executed by a processor cause the processor to perform operations comprising:

receiving a plurality of input medical images of a patient, the plurality of input medical images comprising a query image and one or more candidate images;

encoding the plurality of input medical images into embeddings using a machine learning based encoder network;

performing a medical imaging analysis task by determining at least one of the one or more candidate images as corresponding to the query image based on the embeddings using the machine learning based encoder network, wherein determining at least one of the one or more candidate images as corresponding to the query image based on the embeddings using the machine learning based encoder network comprises:

ranking the embeddings for the one or more candidate images based on a similarity to the embeddings for the query image using the machine learning based encoder network; and outputting results of the medical imaging analysis task.

16. The non-transitory computer readable medium of claim 15, further comprising:

extracting patches from the plurality of input medical images, wherein encoding the plurality of input medical images into embeddings using a machine learning based encoder network comprises:

encoding the patches into the embeddings based on one or more of spatial, temporal, anatomical, cardiac phase, and angulation information extracted from the plurality of input medical images using a transformer-based encoder network.

17. The non-transitory computer readable medium of claim 15, wherein the plurality of input medical images comprises coronary angiography images of the patient.

18. A non-transitory computer readable medium storing computer program instructions, the computer program instructions when executed by a processor cause the processor to perform operations comprising:

receiving a plurality of input medical images of a temporal sequence of medical images of a patient;

extracting patches from the plurality of input medical images;

generating temporal relationships for the patches;

encoding the plurality of input medical images into embeddings using a machine learning based encoder network, wherein encoding the plurality of input medical images into embeddings using a machine learning based encoder network comprises:

encoding the patches, with the temporal relationships, into the embeddings using a transformer-based encoder network;

performing a medical imaging analysis task based on the embeddings, wherein performing a medical imaging analysis task based on the embeddings comprises:

performing the medical imaging analysis task based on the embeddings using a transformer-based decoder network; and outputting results of the medical imaging analysis task.

19. The non-transitory computer readable medium of claim 18, further comprising:

extracting patches from the plurality of input medical images, wherein encoding the plurality of input medical images into embeddings using a machine learning based encoder network comprises:

encoding the patches into the embeddings based on one or more of spatial, temporal, anatomical, cardiac phase, and angulation information extracted from the plurality of input medical images using a transformer-based encoder network.

20. The non-transitory computer readable medium of claim 18, wherein determining at least one of the one or more candidate images as corresponding to the query image based on the embeddings using the machine learning based encoder network further comprises:

generating matching scores between the embeddings using the machine learning based encoder network.

21. The non-transitory computer readable medium of claim 18, wherein the plurality of input medical images comprises coronary angiography images of the patient.

\* \* \* \* \*